United States Patent [19]
Aaronson et al.

[11] Patent Number: 5,792,638
[45] Date of Patent: Aug. 11, 1998

[54] HUMAN RAS-RELATED ONCOGENES UNMASKED BY EXPRESSION CDNA CLONING

[75] Inventors: Stuart A. Aaronson; Andrew Chan, both of New York, N.Y.; Toru Miki, Rockville, Md.

[73] Assignee: The United States of America as represented by the Department of Health and Human Services, Rockville, Md.

[21] Appl. No.: 247,946

[22] Filed: May 24, 1994

[51] Int. Cl.$^6$ .............................. C12N 9/16; C12N 15/01; C12N 15/12; C12Q 1/68
[52] U.S. Cl. .............................. 435/194; 435/6; 536/23.2; 536/24.31
[58] Field of Search ..................... 435/6, 172.1, 172.3, 435/196, 194; 536/23.2, 24.31

[56] References Cited

U.S. PATENT DOCUMENTS 5,234,839  8/1993  McCormick et al. ............. 436/501

FOREIGN PATENT DOCUMENTS

95/32223  11/1995  WIPO .

OTHER PUBLICATIONS

Bos. ras oncogenes in human cancer: a review. Cancer Research. vol.49, pp. 4682–4689, Sep. 1, 1989.

Valencia et al. The ras protein family: evolutionary tree and role of conserved amino acids. Biochemistry. vol.30, No.19, pp. 4637–4648, May 14, 1991.

Barbacid. ras genes. Annual Review of Biochemistry. vol. 56, pp. 779–827, 1987.

AA. Chan, et al.; "A human oncogene of the RAS superfamily unmasked by expression cDNA cloning", PNAS USA 91: 7558–7562 (Aug. 1994).

BB. Saez, et al., "Oncogenic activation of human R–ras by point mutations analogous to those of prototype H–ras oncogenes", Oncogene 9(10): 2977–2982 (Oct. 1994).

CC. Cox, et al., "R–Ras induces malignant, but not morphologic, transformation of NIH3T3 cells", Oncogene 9(11): 3281–3288 (Nov. 1994).

DD. Carboni, et al., "Farnesyltransferase inhibitors are inhibitors of Ras but not R–Ras2/TC21, transformation" Oncogene 10(10): 1905–1913 (May 18, 1995).

D. G. Lowe, et al. "Structure of the Human and Murine R–ras Genes, Novel Genes Closely Related to ras Proto–oncogenes," Cell. vol. 48, pp. 137–148, Jan. 16, 1987.

D. G. Lowe, et al. "Heterologous Expression and Characterization of the Human R–ras Gene Product," Molecular and Cellular Biology, pp. 2845–2856, Aug. 1987.

G. T. Drivas, et al. "Characterization of Four Novel ras–Like Genes Expressed in a Human Teratocarcinoma Cell Line," Molecular and Cellular Biology, pp. 1793–1798, Apr. 1990.

H. B. Muss, et al. "c–erbB–2 Expression and Response to Adjuvant Therapy in Women With Node–Positive Early Breast Cancer," The New England Journal of Medicine, pp. 1260–1266, May 5,1994.

S.M. Graham, et al. "Aberrant Function of the Ras–Related Protein TC21/R–Ras2 Triggers Malignant Transformation," Molecular and Cellular Biology, pp. 4108–4115, Jun. 1994.

*Primary Examiner*—Stephen Walsh
*Assistant Examiner*—Brian Lathrop
*Attorney, Agent, or Firm*—Morgan & Finnegan, L.L.P.

[57] ABSTRACT

The oncogene of the present invention, isolated by expression cloning from a human ovarian cancer is a mutant of TC21. The present invention teaches that ras-related genes not thought to have transforming potential can contribute importantly to cancers which have been refractory to oncogene detection. The present invention teaches that another ras relative gene, R-ras, which was previously reported to lack transforming potential, has transforming capacity as well. Thus, these and other genes similarly related to prototype and activated by analogous mechanisms may be important in the diagnosis and prognosis of certain cancers, as well as be critical in the design of rational approaches to therapy of cancers in which they play a role.

7 Claims, 8 Drawing Sheets

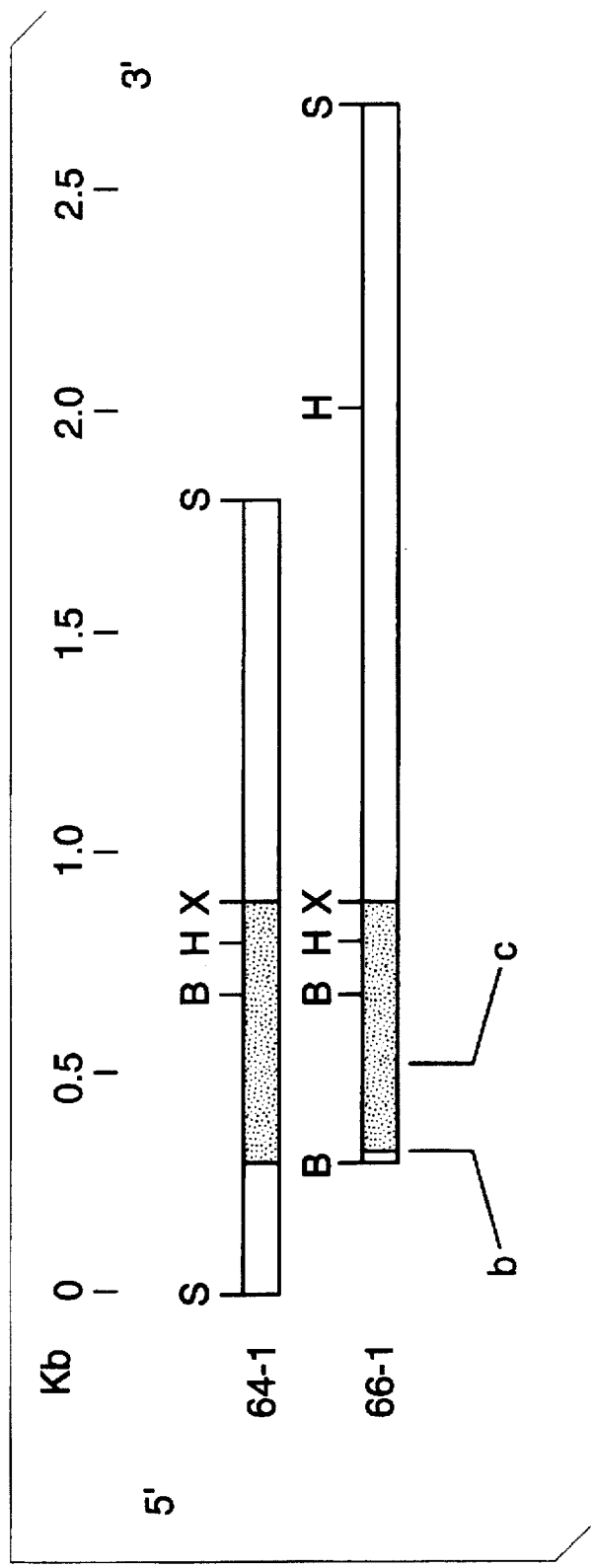

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2336
        ( B ) TYPE: Nucleic Acid
        ( C ) STRANDEDNESS: Double
        ( D ) TOPOLOGY: Linear ( i i ) MOLECULE TYPE: cDNA ( i i i ) HYPOTHETICAL: No ( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: R-ras gene
        ( B ) LOCATION:
        ( C ) IDENTIFICATION METHOD:
        ( D ) OTHER INFORMATION: exon 1, intron A ( x i ) SEQUENCE DESCRIPTION: SEQ ID NO:1:

```
GAATTCGGGT CCCCCCAAGC CAGTGCCCTC GCTCGGATCC                40
AGAATCCTGG GTCCCAGCC  TCTCCAATTC CTGGACCTAA                80
GAGTCCAGGC CCCCGGCTCC CTCCTTTACC GAACCTAGTA               120
CGAAGGAACC TGTCTACCTT CCTCCCTGAC ACCCTCCTCC               160
CCAGGACCCA GGAGTCCACA TCTCCAGCCC CATTTTCTCC               200
TAAGGACCCA GGAGTCTGGG CCCTCTGCTT CCTTCTCCTT               240
CAAGACCCAG AAATCCTGGC CCCAGGCTCT TCATGACCCA               280
GGCATCCCTA CTTGGGCGAG CTGGCTCATG GATTAGGAAT               320
GCAGTGATCT CACGGCCCCT CCCTGCCCCG TTACCCTGCT               360
GTCCCCTCT  AGGGCCCAC  TCTCCTCCCA GTCTGTCTTC               400
CGCTTGGCTG GGACAGCGGG AACCGGAAGC CTGGGTCCCT               440
TAGCGGGCGG AGACTCTAGC TTCTAACCCA GACGCCGGGG               480
TCGAAAGCTT GGCTAGGATC CCAGGAGGGA GGTGGAGCTA               520
CTCCTCAAAA CCTGCTGCTT CCTCGGAGCG CCCTATATAC               560
GGCCGCGCGC GCGAGTCGAC GAGCTCCGCC TACCATACTA               600
AGGCCTCGGA GACGATGCCC CAAGCAGCAG TGTCACAGGG               640
GTCCTTATTT GCATAGCCCC TCCCTGAGG  AACTTTCCGC               680
```

| | | | | |
|---|---|---|---|---|
| CCCGTCTGCT | GAAAGAATAA | ATTCTTATTA | GCATAGCCAC | 720 |
| GCCCACAGAC | CGCCCTCCCG | CTGAGAGCGC | GTGGCGCCGC | 760 |
| TCAGGGCAAA | GCACAGGTCT | CTCATTAGCA | TAGCCCCGCC | 800 |
| TCATTCGGAA | TTCCCCTTCG | CAGCGAACGC | CGTTCCCTTT | 840 |
| CCCTTATTAA | CATAGCTCCT | CCCTTTCTTT | GGCCCGTCCC | 880 |
| CCTCCTTAAG | TGTCCGGAGA | CGCGAGCCCT | CCTTGCCAGA | 920 |
| GCTCATGATT | ATGCAGTAGC | CTCATTAGCG | TAGCCCGCCC | 960 |
| CCCCGGGTCC | CGCCCGGCTC | CCCCGCAGGC | GGTAGCGAAG | 1000 |
| GCAGCAGCAG | CGGTGGCGAC | ATGAGCAGCG | GNNNGGCGTC | 1040 |
| CGGGACAGGG | CGGGGGCGGC | CCCGGGGCGG | GGGACCTGGG | 1080 |
| CCCGGGGACC | CCCCGCCCAG | CGAGACACAC | AAGCTGGTGG | 1120 |
| TCGTGGGCGG | CGGCGGCGTG | GGCAAGAGCG | CGCTGACCAT | 1160 |
| CCAGTTCATC | CAGGTAGTGG | GCCCTCACCC | GGGAGGTGTC | 1200 |
| CCCCGGGACC | CAGAACTGAG | CCTTGGGGGG | ATCCCCGAGA | 1240 |
| CCCCTTTTCC | CCCTTGACCC | ATCACTGAGA | CCCTCCTATA | 1280 |
| AGGCCCTCTA | ATCTTAAAAG | ATCCCCACAG | ATTGTAACCT | 1320 |
| AAACTCTTGG | AGAGCCTCCA | TCCCTGCAC | GGGGGACCCT | 1360 |
| TCCTTCTGCA | CTCGCATCCC | GAGACCCACT | ATTCCCTCTC | 1400 |
| CCAGTGCCTA | AGACCCCGCT | TACCTGCTGA | CCTGGCTTTG | 1440 |
| AGCACCTCCT | GGGAGCATGC | TAAATACAAA | ATACTCACCC | 1480 |
| CATTCGGACC | CTAAGCACTC | CCAGGACCCC | CACCACGCCC | 1520 |
| TTGGTGCCAC | CTTCCACCAC | CCTGAGCCCT | ATCTCCCCA | 1560 |
| AATCCCAGTC | CCCAACTTCC | CCTCTAAGCC | ATTGAGAGCC | 1600 |
| TTCCTGGGAG | AATGCCAGTG | CCCAGCACTT | TGAGATTCCA | 1640 |
| CCACGTTCGA | TTCTTTTTTT | TCTTTTTTTT | TTTTTTTGA | 1680 |
| GACAGAGTCT | CACTCACTCT | GTCACCCAGG | CTGGAGTGCG | 1720 |
| GTGGAGTGCA | GTGGTGCGAT | GTTGGCTCAC | TGCAACCTCT | 1760 |
| GCCTCCTGGA | TTCAAGCAAT | TCTCCTGCCT | CAGCCTCCCA | 1800 |
| AGTAGCTGAG | ACTACAGGCG | AGTGCACCAT | GCCTGGCTAA | 1840 |
| TTTTTGTATT | TTTTAGTAGA | GACGGGGTTT | CACCATATTG | 1880 |
| GACTGGTCTC | GAACTCCTGA | CCTCGTGATC | GGCCTGCCTT | 1920 |
| GGACTCCCAA | AGTGCTGGGA | TTACAGGCAT | GAGCCACCGT | 1960 |
| GCCCGGCCCC | ACGTTTGATT | CTTAGCCCCT | TCCATGACTG | 2000 |
| CCCCCAGAAT | CTAGAAATTC | TACCCAGACC | CTGGCCCTGA | 2040 |
| GACTCTTCTG | GGACTACCCA | GTCCTAAGAG | AGTCCTGCTC | 2080 |
| TCCGACCCGA | GATTTAAAAA | GACATCCTGC | CCCTTGGCCA | 2120 |
| TTCCAGAAAT | CTCCAAGACC | CCAAGTCCTG | ACAATCCCCC | 2160 |
| ATTCCCGGAG | GCCCAAACCT | CCACTCTCCC | ACCCACCCC | 2200 |
| CAAGGAAAAC | CAGCCCCTCC | TCCATCCCAT | GCTTTCTCCG | 2240 |
| CTGCAACTCC | CTGAGCCCCT | CTCAGAAACC | CTGAATAGCT | 2280 |

|  |  |  |  |  |
|---|---|---|---|---|
| CTCAAATCAT | CTCCATGGAA | GAAGCCCCCA | GATTCTTGGC | 2320 |
| ACCCCCAGAA | AGATCT |  |  | 2336 |

( 2 ) INFORMATION FOR SEQ ID NO:2:

( i ) SEQUENCE CHARACTERISTICS:
        ( A ) LENGTH: 3350
        ( B ) TYPE: Nucleic acid
        ( C ) STRANDEDNESS: Double
        ( D ) TOPOLOGY: Linear ( i i ) MOLECULE TYPE: cDNA ( i i i ) HYPOTHETICAL: No ( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: Human R-ras gene
        ( B ) LOCATION:
        ( C ) IDENTIFICATION METHOD:
        ( D ) OTHER INFORMATION: exons 2- 6.

( x i ) SEQUENCE DESCRIPTION: SEQ ID NO:2:

|  |  |  |  |  |
|---|---|---|---|---|
| AGCTACCCAA | AGAGAAGGGG | ACAGAGACCC | AGAGAGAGAG | 40 |
| AGTAATAGAG | ACTCAGAGAG | ACAGAGGGGA | CAGAGACCCA | 80 |
| GAGAAAAGGG | GGCAGAGACC | CAGCAACAAG | GACAGACATC | 120 |
| TGGAGAGAGA | GAGAAGGACA | GGGCAGGGCG | CAGTGGCTCA | 160 |
| CATCTGTAAT | CCCAGCACTT | TGGGAGACCC | AGGCGGGCGG | 200 |
| ATCACCTGAG | GTCAGGAGTT | CGAGACCAGC | CTGACCAACA | 240 |
| CAGCCTGACC | AACACATCTC | TACTAAAAAT | ACAAAATTAG | 280 |
| CCAGGTGTGG | TGGCGCATGC | CTGTAATCCC | AGCTACTTGG | 320 |
| GAGGCTGAGG | CAGGAGAATC | TCTTGAACCC | AGGAGGCAGA | 360 |
| GGTTGCAGTG | AGCCGAGATC | TCGCCATTGC | ACTCCAGCCT | 400 |
| GTGCAACAAG | AGCGAAACTC | CGTCTCAAAA | AAAAAAAAA | 440 |
| AAAAAAAAG | ATTCAGAGAG | ACAGACGGGA | CAGAGACCCA | 480 |
| GAGAAAGGG | GGCAGAGACC | CAGCAACAGG | GACAGACATT | 520 |
| TAGAGAGAGA | GGGACAGAGA | CTGAGAGAGG | CATCCCAAGG | 560 |
| GCAGGGCTTC | GTCCTGTCTG | CCGGGGCACT | GCAGTAACTA | 600 |
| TCCTCTCCCC | ACCCCGCCAG | TCCTACTTCG | TGTCTGACTA | 640 |
| CGACCCCACT | ATTGAGGACT | CCTACACGAA | GATCTGCAGT | 680 |
| GTGGATGGCA | TCCCAGCCCG | GCTGGACAGT | GAGGGCGGCA | 720 |
| AGGATGGATG | ATGGATGGGG | GTGGTGTCAG | TGGGGGCTGA | 760 |
| GTGCTCTTGG | GGGTGACTGC | GGGGAGCCTG | GTCCCACAA | 800 |
| TGGCCCCTCT | CCCTGTCTCT | GCAGTCCTGG | ACACCGCGGG | 840 |
| CNNNGAAGAG | TTCGGGGCCA | TGAGAGAGCA | GTACATGCGT | 880 |

| | | | |
|---|---|---|---|
| GCTGGCCACG | GCTTCCTGCT | GGTGTTCGCC | ATTAATGACC | 920 |
| GGCAGAGGTG | ACAGGGGTTA | CTGGTGGCGG | AGCAGTGGGT | 960 |
| GGGTGTGGGG | AGGACCTGGG | CTCTGCAGCT | GGCTGGACCT | 1000 |
| CATGCCTCCG | GCTTCACTCG | CAGTTTCAAC | GAGGTGGGCA | 1040 |
| AGCTCTTCAC | GCAGATTCTG | CGGGTCAAGG | ACCGCGACGA | 1080 |
| CTTCCCCGTT | GTGTTGGTCG | GGAACAAGGC | AGATCTGGAG | 1120 |
| TCACAGCGCC | AGGTTCGGGA | CACCCCTCTT | TCTGGGGACC | 1160 |
| CCATCTCAGT | CTGGGAGGCT | CCTTCCAGCA | CACCTGTCCC | 1200 |
| CCATCAGCAT | CCTCCTCTGT | TCCTGCAGTG | CTGCGACTGC | 1240 |
| CACTGTCACA | CAGCTCACCT | AGATGGGTTA | CCCCCAAACT | 1280 |
| GGACCTTCAG | GGTCCCCGGC | ATCACCGAGC | AGAGGGCCTA | 1320 |
| GCATGCAAGT | GTCCTCAGGA | GAGGCTGCTG | GACGGAACAA | 1360 |
| AGGACATTCA | CCCCCCGTCC | GCCAGCTCTC | TTTGCCCCTT | 1400 |
| CCTCGCATTC | CTCCCTTCCA | GCCAACCTCC | CACCAGCCCC | 1440 |
| AGCACCTCCC | CTGCTCATGG | CCGGCCCCCT | CCATGGCTCC | 1480 |
| CCAGTTCCTC | CCCAGGTGCC | AGATGCCCCG | CACAGTTGCG | 1520 |
| CCCCTCCTTT | CCCTGCTCCC | ATCACTTCCC | CCACAACGAT | 1560 |
| TTCCACACAG | AACTCATCCA | TCTGGCAAAG | GCTCTGGGGA | 1600 |
| TTTCCAGGCT | TTGGGGTTCC | GCCTGCCTCT | GCCGGGAACA | 1640 |
| CCCTGACTTC | CCTGCCTGCC | CACTCCTGGT | TATCTAAGGC | 1680 |
| ATAGCAGGGC | AAGTGCCCAC | GAAGCCTGCC | CCCATCCCTT | 1720 |
| ACTTAGAAGA | CACCAAGCCC | CTGCGGCATC | TCCCTCCATA | 1760 |
| ATCTCTCAGG | AGCTCTTCCT | CTTTGAGTTC | TCACAGTGGG | 1800 |
| TCACCTCTCC | TAGAGTATCC | AGCCTGCCTG | TCTGTCTCTC | 1840 |
| TGGCTGCGGT | CACCCTGAGT | GCAGGGACCT | GACTCCCCG | 1880 |
| TGTCCCCCCT | ACCCCAGGT | CCCCCGATCA | GAAGCCTCTG | 1920 |
| CCTTCGGCGC | CTCCCACCAC | GTGGCCTACT | TTGAGGCCTC | 1960 |
| GGCCAAACTG | CGTCTCAACG | TGGACGAGGC | TTTTGAGCAG | 2000 |
| CTGGTGCGGG | CTGTCCGGTG | AGCCAAGTCC | CCTTCCTGTC | 2040 |
| GTCCTTGTCC | CCAGCCCTTC | CACTCCAAAC | TCACTGGCGT | 2080 |
| TTTCCCACAG | GAAATACCAG | GAACAAGAGC | TCCCACCGAG | 2120 |
| CCCTCCCAGT | GCCCCAGGA | AGAAGGGCGG | GGGCTGCCCC | 2160 |
| TGCGTCCTCC | TGTAGCCCAG | GCAAGAGAGA | AGCAACCACC | 2200 |
| ACAAGCTCTC | GGGACTAGCT | GCCTTCGCAC | CTTGCTGTGT | 2240 |
| GACCTGAGGC | CCTCACTGAG | CCTCAATTTC | CTCATCTGGG | 2280 |
| TCTCCCAGGA | CACATCACAT | ACCCACCCTT | ACTTCCTGGC | 2320 |
| CTCTTCTGGG | CTACTGCCAC | TGTGTGCCTT | CTGCCAACGC | 2360 |
| CTCCTGTCCC | CACCTAAGCC | TGGTGGGGGT | GAGGGGCTCC | 2400 |
| GGGTCACTGC | TGTATATAAC | TCCCCTCCCC | CAGAAAAATA | 2440 |
| AATGTCACTG | CCAACGTCAG | GAGGTGCTTT | CTAAAAAGGT | 2480 |

| | | | | |
|---|---|---|---|---|
| AATGAGGGTC | GGGCACTGTG | GCTCACTCCT | GTAATCGCAG | 2520 |
| CATTTTGGGA | GGCCAATGCG | GGAGGACCGC | TTGAGTCCAG | 2560 |
| GAGTTTTTGA | CCAGCCTGGG | CAGCATAGCG | AGACCCCAT | 2600 |
| CTCTTAAAAA | AAAAGGGTGG | GGGAATGAAC | TCTGGGAAGG | 2640 |
| TGAACGAATT | CATGCCACAT | AGCGAGACCC | CATCTCTACA | 2680 |
| ACAAAATGAA | AAATTAGCCA | AGTGTGCACT | CGTAGTCCCA | 2720 |
| GCTACTTGGG | AGGCTGAGGC | AGGAGGATTG | CTTGAGCCCA | 2760 |
| GGAGGTTGAG | GCTACAGAGT | TGTGATCACG | CGACTGCACT | 2800 |
| CCAGCCTGGG | CAACACAGTG | ACACCCTGTC | TCAAATAAAT | 2840 |
| AAATAAAATG | TAAAAAACGA | AGTGTTCCTA | GGACACAGAT | 2880 |
| GGGCTTTGGG | TATCCAGACT | GAAGTGTGTC | ATCCATTTAC | 2920 |
| CCACTGTGGC | CTTAAGACAC | CCAACACTTC | TGCTTCTCCC | 2960 |
| AGGACAGAAT | AGGGGGTTGG | ATGGGGATG | TCCACACTGA | 3000 |
| CCCCAAATTG | GATTAAGTGT | TTAGATTCAG | ATTTCAGTGC | 3040 |
| TACTGGGAAC | TTTCTGAAAA | TGAGGACTTG | CCAGACGGCT | 3080 |
| GCTTGGACAC | CATTCCACCC | ACCTGTCCCT | TCTCGATATA | 3120 |
| CATTGAAGGT | GAGAGTGGGA | CAGGCAGGGT | TTGTAGCAGT | 3160 |
| TGCTCCCTGT | CTCTATTTTT | GTAGACAGAG | TCTAGCTCTT | 3200 |
| GCCCAGGCTG | GTCTCAAACT | CCTGGCCTCA | AGTGATCCAC | 3240 |
| CCATTTCGGT | CTCCCAAAGT | ACTGGGCTTA | CAAGCGTGAG | 3280 |
| CTACCACACC | CAGCAGCTGA | GTTGCTGCCT | GTCTCCAATG | 3320 |
| TCCTAGAACG | TTCTATTGGA | ATGTTCTAGA | | 3350 |

( 2 ) INFORMATION FOR SEQ ID NO:3:

( i ) SEQUENCE CHARACTERISTICS:
        ( A ) LENGTH: 218
        ( B ) TYPE: Amino acid
        ( C ) STRANDEDNESS:
        ( D ) TOPOLOGY: Unknown ( i i ) MOLECULE TYPE: Protein ( i i i ) HYPOTHETICAL: No ( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: R-ras gene product
        ( B ) LOCATION:
        ( C ) IDENTIFICATION METHOD:
        ( D ) OTHER INFORMATION:

( x i ) SEQUENCE DESCRIPTION: SEQ ID NO:3:

Met Ser Ser Gly Ala Ala Ser Gly Thr Gly Arg Gly Arg
            5                  10

Pro Arg Gly Gly Gly Pro Gly Pro Gly Asp Pro Pro Pro

|   |   |   | 15 |   |   |   | 20 |   |   |   | 25 |   |
|---|---|---|---|---|---|---|---|---|---|---|---|---|
| Ser | Glu | Thr | His | Lys | Leu | Val | Val | Gly | Gly | Xaa | Gly |
|   |   |   | 30 |   |   |   | 35 |   |   |   |   |   |

| Val | Gly | Lys | Ser | Ala | Leu | Thr | Ile | Gln | Phe | Ile | Gln | Ser |
| 40 |   |   |   |   | 45 |   |   |   |   | 50 |   |   |

| Tyr | Phe | Val | Ser | Asp | Tyr | Asp | Pro | Thr | Ile | Glu | Asp | Ser |
|   |   | 55 |   |   |   | 60 |   |   |   |   |   | 65 |

| Tyr | Thr | Lys | Ile | Cys | Ser | Val | Asp | Gly | Ile | Pro | Ala | Arg |
|   |   |   |   | 70 |   |   |   |   | 75 |   |   |   |

| Leu | Asp | Ile | Leu | Asp | Thr | Ala | Gly | Xaa | Glu | Glu | Phe | Gly |
|   | 80 |   |   |   |   | 85 |   |   |   |   | 90 |   |

| Ala | Met | Arg | Glu | Gln | Tyr | Met | Arg | Ala | Gly | His | Gly | Phe |
|   |   |   | 95 |   |   |   | 100 |   |   |   |   |   |

| Leu | Leu | Val | Phe | Ala | Ile | Asn | Asp | Arg | Gln | Ser | Phe | Asn |
| 105 |   |   |   |   | 110 |   |   |   |   | 115 |   |   |

| Glu | Val | Gly | Lys | Leu | Phe | Thr | Gln | Ile | Leu | Arg | Val | Lys |
|   |   | 120 |   |   |   |   | 125 |   |   |   |   | 130 |

| Asp | Arg | Asp | Asp | Phe | Pro | Val | Val | Leu | Val | Gly | Asn | Lys |
|   |   |   |   | 135 |   |   |   |   | 140 |   |   |   |

| Ala | Asp | Leu | Glu | Ser | Gln | Arg | Gln | Val | Pro | Arg | Ser | Glu |
|   | 145 |   |   |   |   | 150 |   |   |   |   | 155 |   |

| Ala | Ser | Ala | Phe | Gly | Ala | Ser | His | His | Val | Ala | Tyr | Phe |
|   |   |   |   | 160 |   |   |   | 165 |   |   |   |   |

| Glu | Ala | Ser | Ala | Lys | Leu | Arg | Leu | Asn | Val | Asp | Glu | Ala |
| 170 |   |   |   |   | 175 |   |   |   |   | 180 |   |   |

| Phe | Glu | Gln | Leu | Val | Arg | Ala | Val | Arg | Lys | Tyr | Gln | Glu |
|   |   | 185 |   |   |   |   | 190 |   |   |   |   | 195 |

| Gln | Glu | Leu | Pro | Pro | Ser | Pro | Ser | Ala | Pro | Arg | Lys |
|   |   |   |   | 200 |   |   |   | 205 |   |   |   |

| Lys | Gly | Gly | Gly | Cys | Pro | Cys | Val | Leu | Leu |
|   | 210 |   |   |   |   | 215 |   |   |   |

( 2 ) INFORMATION FOR SEQ ID NO:4:

( i ) SEQUENCE CHARACTERISTICS:
        ( A ) LENGTH: 204
        ( B ) TYPE: Amino acid
        ( C ) STRANDEDNESS: Single
        ( D ) TOPOLOGY: Unknown ( i i ) MOLECULE TYPE: Protein ( i i i ) HYPOTHETICAL: No ( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: TC21 gene product
        ( B ) LOCATION:
        ( C ) IDENTIFICATION METHOD:
        ( D ) OTHER INFORMATION:

( x i ) SEQUENCE DESCRIPTION: SEQ ID NO:4:

Met Ala Ala Ala Gly Trp Arg Asp Gly Ser Gly Gln Glu

```
         1                       5                            10
    Lys  Tyr  Arg  Leu  Val  Val  Val  Gly  Gly  Xaa  Gly  Val  Gly
              15                      20                      25

Lys  Ser  Ala  Leu  Thr  Ile  Gln  Phe  Ile  Gln  Ser  Tyr  Phe
                   30                      35

Val  Thr  Asp  Tyr  Asp  Pro  Thr  Ile  Glu  Asp  Ser  Tyr  Thr
    40                       45                      50

Lys  Gln  Cys  Val  Ile  Asp  Asp  Arg  Ala  Ala  Arg  Leu  Asp
              55                      60                           65

Ile  Leu  Asp  Thr  Ala  Gly  Xaa  Glu  Glu  Phe  Gly  Ala  Met
                        70                      75

Arg  Glu  Gln  Tyr  Met  Arg  Thr  Gly  Glu  Gly  Phe  Leu  Leu
         80                       85                           90

Val  Phe  Ser  Val  Thr  Asp  Arg  Gly  Ser  Phe  Glu  Glu  Ile
                   95                      100

Tyr  Lys  Phe  Gln  Arg  Gln  Ile  Leu  Arg  Val  Lys  Asp  Arg
    105                      110                     115

Asp  Glu  Phe  Pro  Met  Ile  Leu  Ile  Gly  Asn  Lys  Ala  Asp
              120                     125                      130

Leu  Asp  His  Gln  Arg  Gln  Val  Thr  Gln  Glu  Glu  Gly  Gln
                        135                     140

Gln  Leu  Ala  Arg  Gln  Leu  Lys  Val  Thr  Tyr  Met  Glu  Ala
         145                     150                          155

Ser  Ala  Lys  Ile  Arg  Met  Asn  Val  Asp  Gln  Ala  Phe  His
                   160                     165

Glu  Leu  Val  Arg  Val  Ile  Arg  Lys  Phe  Gln  Glu  Gln  Glu
    170                      175                     180

Cys  Pro  Pro  Ser  Pro  Glu  Pro  Thr  Arg  Lys  Glu  Lys  Asp
              185                     190                      195

Lys  Lys  Gly  Cys  His  Cys  Val  Ile  Phe
                        200
```

( 2 ) INFORMATION FOR SEQ ID NO:5:

( i ) SEQUENCE CHARACTERISTICS:
        ( A ) LENGTH: 615
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( v i ) ORIGINAL SOURCE:
        ( A ) ORGANISM: Human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: TC21 gene
        ( B ) LOCATION:
        ( C ) IDENTIFICATION METHOD:
        ( D ) OTHER INFORMATION:

( x i ) SEQUENCE DESCRIPTION: SEQ ID NO:5:

```
ATGGCCGCGG   CCGGCTGGCG   GGACGGCTCC   GGCCAGGAGA                              40
```

| | | | | |
|---|---|---|---|---|
| AGTACCGGCT | CGTGGTGGTC | GGCGGGGGCG | GCGTGGGCAA | 80 |
| GTCGGCGCTC | ACCATCCAGT | TCATCCAGTC | CTATTTTGTA | 120 |
| ACGGATTATG | ATCCAACCAT | TGAAGATTCT | TACACAAAGC | 160 |
| AGTGTGTGAT | AGATGACAGA | GCAGCCCGGC | TAGATATTTT | 200 |
| GGATACAGCA | GGANNGAAG | AGTTTGGAGC | CATGAGAGAA | 240 |
| CAGTATATGA | GGACTGGCGA | AGGCTTCCTG | TTGGTCTTTT | 280 |
| CAGTCACAGA | TAGAGGCAGT | TTTGAAGAAA | TCTATAAGTT | 320 |
| TCAAAGACAG | ATTCTCAGAG | TAAAGGATCG | TGATGAGTTC | 360 |
| CCAATGATTT | TAATTGGTAA | TAAAGCAGAT | CTGGATCATC | 400 |
| AAAGACAGGT | AACACAGGAA | GAAGGACAAC | AGTTAGCACG | 440 |
| GCAGCTTAAG | GTAACATACA | TGGAGGCATC | AGCAAAGATT | 480 |
| AGGATGAATG | TAGATCAAGC | TTTCCATGAA | CTTGTCCGGG | 520 |
| TTATCAGGAA | ATTTCAAGAG | CAGGAATGTC | CTCCTTCACC | 560 |
| AGAACCAACA | CGGAAAGAAA | AAGACAAGAA | AGGCTGCCAT | 600 |
| TGTGTCATTT | TCTAG | | | 615 |

( 2 ) INFORMATION FOR SEQ ID NO:6:

( i ) SEQUENCE CHARACTERISTICS:
        ( A ) LENGTH: 24
        ( B ) TYPE: Nucleic acid
        ( C ) STRANDEDNESS: Unknown
        ( D ) TOPOLOGY: Unknown ( i i ) MOLECULE TYPE: oligonucleotide ( i i i ) HYPOTHETICAL: No ( i x ) FEATURE:
        ( A ) NAME/KEY: primer A
        ( B ) LOCATION:
        ( C ) IDENTIFICATION METHOD:
        ( D ) OTHER INFORMATION:

( x i ) SEQUENCE DESCRIPTION: SEQ ID NO:6:

| | | |
|---|---|---|
| ATAGATGACA | GAGCAGCCCG GCTA | 24 |

( 2 ) INFORMATION FOR SEQ ID NO:7:

( i ) SEQUENCE CHARACTERISTICS:
        ( A ) LENGTH: 24
        ( B ) TYPE: Nucleic acid
        ( C ) STRANDEDNESS: Unknown
        ( D ) TOPOLOGY: Unknown ( i i ) MOLECULE TYPE: oligonucleotide ( i i i ) HYPOTHETICAL: No ( i x ) FEATURE:
        ( A ) NAME/KEY: primer B
        ( B ) LOCATION:
        ( C ) IDENTIFICATION METHOD:
        ( D ) OTHER INFORMATION:

( x i ) SEQUENCE DESCRIPTION: SEQ ID NO:7:

| | | |
|---|---|---|
| GATAGAGGCA | GTTTTGAAGA AATC | 24 |

( 2 ) INFORMATION FOR SEQ ID NO:8:

( i ) SEQUENCE CHARACTERISTICS:
          ( A ) LENGTH: 31
          ( B ) TYPE: Nucleic acid
          ( C ) STRANDEDNESS: Unknown
          ( D ) TOPOLOGY: Unknown ( i i ) MOLECULE TYPE: oligonucleotide ( i i i ) HYPOTHETICAL: No ( i x ) FEATURE:
          ( A ) NAME/KEY: p5
          ( B ) LOCATION:
          ( C ) IDENTIFICATION METHOD:
          ( D ) OTHER INFORMATION: BamH1-tagged (+)
                   primer ( x i ) SEQUENCE DESCRIPTION: SEQ ID NO:8:

AAAGGATCCA TGAGCAGCGG GGCGGCGTCC G            3 1

( 2 ) INFORMATION FOR SEQ ID NO:9:

( i ) SEQUENCE CHARACTERISTICS:
               ( A ) LENGTH: 30
               ( B ) TYPE: Nucleic acid
               ( C ) STRANDEDNESS: Unknown
               ( D ) TOPOLOGY: Unknown ( i i ) MOLECULE TYPE: oligonucleotide ( i i i ) HYPOTHETICAL: No ( i x ) FEATURE:
               ( A ) NAME/KEY: p10
               ( B ) LOCATION:
               ( C ) IDENTIFICATION METHOD:
               ( D ) OTHER INFORMATION: EcoR1-tagged (-)
                        primer ( x i ) SEQUENCE DESCRIPTION: SEQ ID NO:9:

AAAGAATTCC TACAGCAGGA CGCAGGGGCA            3 0

( 2 ) INFORMATION FOR SEQ ID NO:10:

( i ) SEQUENCE CHARACTERISTICS:
               ( A ) LENGTH: 25
               ( B ) TYPE: Nucleic acid
               ( C ) STRANDEDNESS: Unknown
               ( D ) TOPOLOGY: Unknown ( i i ) MOLECULE TYPE: oligonucleotide ( i i i ) HYPOTHETICAL: No ( i x ) FEATURE:
               ( A ) NAME/KEY:
               ( B ) LOCATION:
               ( C ) IDENTIFICATION METHOD:
               ( D ) OTHER INFORMATION: position 38
                        complementary mutant oligonucleotide ( x i ) SEQUENCE DESCRIPTION: SEQ ID NO:10:

TCGTGGGCGG CGTCGGCGTG GGCAA            2 5

( 2 ) INFORMATION FOR SEQ ID NO:11:

( i ) SEQUENCE CHARACTERISTICS:
               ( A ) LENGTH: 24
               ( B ) TYPE: Nucleic acid
               ( C ) STRANDEDNESS: Unknown
               ( D ) TOPOLOGY: Unknown ( i i ) MOLECULE TYPE: oligonucleotide

```
    ( i i i ) HYPOTHETICAL: No ( i x ) FEATURE:
            ( A ) NAME/KEY:
            ( B ) LOCATION:
            ( C ) IDENTIFICATION METHOD:
            ( D ) OTHER INFORMATION: position 87
                    complementary mutant oligonucleotide ( x i ) SEQUENCE DESCRIPTION: SEQ ID NO:11:

GACACCGCGG GCCTGGAAGA GTTC                                           2 4
```

HUMAN RAS-RELATED ONCOGENES UNMASKED BY EXPRESSION CDNA CLONING

FIELD OF THE INVENTION

The present invention relates to a novel class of oncogenes. In particular, a novel oncogene, mutant TC21 has been associated with human ovarian carcinoma cells. Mutations of R-ras have also been found to be oncogenic. The novel oncogenes of the present invention are useful in detecting transformed cells in tumors and tissues not previously associated with an activated oncogene.

BACKGROUND OF THE INVENTION

A family of small G-proteins encoded by H-, K-, and N-ras is frequently activated as oncogenes in a wide array of human tumors (Bos, 1989). Activation is generally due to point mutation at one of two major sites, position 12 or 61, within the coding sequence. These mutations cause the molecule to be constitutively in the GTP bound (active) rather than GDP bound (inactive) state (Barbacid, 1989). In normal cells, these proteins are coupled to growth factor signaling pathways and appear to cause proliferation or differentiation depending on the cell type (Chardin, 1991). Over the past several years, cloning efforts by many laboratories have greatly expanded the number of known ras-related proteins, some of which like Rho and Rac, are coupled to signaling pathways related to cell motility (Ridley & Hall, 1992; Ridley et al., 1992). Others, including the Rab proteins are involved in intracellular vesicular transport (Novick & Brennwald, 1993).

Three ras-related molecules, R-ras, K-rev-1/rap and TC21, within the ras superfamily are more closely related to ras than to either Rho or Rab subfamilies. TC21 has recently been cloned by means of degenerate PCR primers but is otherwise uncharacterized (Drivas, et al., 1990). The human R-ras gene was initially cloned by low-stringency hybridization method using a viral H-ras cDNA as probe (Lowe et al., 1987). R-ras has been thought to be non-transforming since efforts to detect transforming potential by introduction of ras-activating mutations were unsuccessful (Lowe & Goeddel, 1987). Recent studies have demonstrated R-ras interacts with the BCL-2 product involved in a signaling pathway that intervenes with apoptosis (Fernandez-Sarabia & Bischoff, 1993). K-rev-1/rap, was initially detected as a suppressor of ras transforming function (Kitayama et al., 1989).

Three previously identified ras genes with transforming potential include H-, K- and N-ras. Whereas H-, K- and N-ras p21 proteins share 75% amino acid sequence identity, this similarity increases to greater than >97% when their putative N-terminal catalytic domains (positions 5 to 120) are compared. In contrast, TC21 shows 56% overall similarity and only 70% relatedness in the conserved catalytic domain. Structurally, TC21 also contains an N-terminal 11 amino acid extension, which would result in a predicted 23 kD product rather than the 21 kd proteins observed for H-, K- as well as N-ras. Of note, TC21 is more closely related to H-, K- and N-ras than the human R-ras gene product with 64% identity throughout, and 76% similarity in the most conserved domain. R-ras was initially identified by low stringency hybridization using a viral H-ras probe (Lowe, et al., 1987). Yet, efforts to mutationally activate R-ras as an oncogene in vitro were unsuccessful (Lowe & Goeddel, 1987). Thus, it would not be possible to predict the oncogenic potential of TC21 by comparison of its overall similarity or function with known ras-related genes.

Previously identified ras oncogenes have been implicated in a wide array of human malignancies. Greater than 90% of pancreatic carcinomas and more than 50% of colon carcinomas exhibit activating mutations of H- or K-ras alleles (Bos, 1989). Such oncogenes have also been identified in a variety of other carcinomas. In contrast, N-ras oncogenes seem to be preferentially observed in mesenchymal and hematopoietic malignancies (Bos, 1989). Evidence from experimental models indicates that ras oncogenes may be responsible for initiation of the malignant process as well as play important roles in later steps of tumor progression of cancers in which an activated ras protein has been identified to exist (Barbacid, 1987). Oncogenes have yet to be commonly detected in many human tumors. These include ovarian, breast and prostate tumors as well as hepatomas and melanomas.

SUMMARY OF THE INVENTION

As an approach to identify new human oncogenes, the present invention has generated an expression cDNA library from an ovarian carcinoma line. The present invention relates to the detection of a potent transforming gene product. The transforming gene product was identified as mutant TC21 protein, having a single point mutation substituting glutamine with leucine at position 72. TC21 is a recently cloned member of the ras gene superfamily. While the mutant TC21 cDNA clone possessed high transforming activity, the ovarian tumor genomic DNA which contained the mutated TC21 allele failed to induce transformed foci. Thus, by the use of a non-conventional expression cDNA cloning system, it was possible to identify and isolate a new human oncogene that has evaded detection by cloning techniques within in the art.

Based on the finding that an oncogenic form of TC21 exists, the present invention also relates to the generation of various point mutations to a close relative, R-ras, for expression study in rodent fibroblasts. Mutations introduced to the R-ras gene at positions 38 and 87 induced morphological transformation in NIH/3T3 cells at high frequency. NIH/3T3 cells transfected with mutant R-ras plasmids grew well in soft agar and were tumorigenic in animals. The 4.6 and 1.2 kb transcripts of R-ras were ubiquitously expressed in all human tissues examined. The present invention provides further biological evidence that R-ras gene can indeed synergize with c-raf-1 gene in inducing cellular transformation. In fact, cooperation between wild-type H-ras and c-raf-1 genes in transforming NIH/3T3 cells has previously been reported (Cuadrado et al., 1993). In the instant invention, the use of wild-type R-ras gene was insufficient to register a cooperative effect and expression of the oncogenic R-ras mutant at position 38 ("R-ras$^{val38}$") construct was necessary to produce a similar result in activating the transforming pathway in NIH/3T3 cells.

Based upon the finding that the proteins of the present invention are oncogenic, mutations clustered within these regions also exhibit oncogenic characteristics. For TC21, mutations clustered around codon positions 23 to 75 will result in a mutant having oncogenic properties. For R-ras, mutations clustered around codon positions 3 to 87 will have oncogenic activity. Analogous regions of other ras proteins have been demonstrated to produce oncogenically active mutants of ras (Bos, 1989).

The present invention relates to methods of diagnosing cancers and cell transformations by detection of mutant forms of R-ras or TC21 or detection of mutant forms of the corresponding genes. The novel oncogenes of the present invention are important in serving as tumor markers, allowing relevant cancers to be diagnosed and monitored in prognosis of disease progression. The invention further relates to detecting mutant TC21 or the mutant TC21 gene in ovarian tissue to determine whether said tissue is transformed. The present invention also relates to a kit for diagnosing certain types of cancers by determination of elevated levels of mutant TC21 and/or R-ras, or by expression of mutant forms of the corresponding genes.

The present invention also relates to methods of controlling or inhibiting the transforming capability of the novel oncogenes of the present invention.

DESCRIPTION OF THE DRAWINGS

FIGS. 2A, 2B & 2C. Physical characterization of transforming cDNAs. (2A) Schematic representation of the 1.7 kb and 2.4 kb cDNA inserts of 64-1 and 66-1 plasmids, respectively. Open reading frames encoding the TC21 gene product are indicated by filled boxes and 5' and 3' untranslated regions are represented by open boxes. Abbreviations of restriction enzymes are: S (SalI), B (BglII), H (HindIII) and, X (XbaI). (2B) Sequence disparities in N-terminal coding regions of the TC21 (Drivas, et al., 1990) and 66-1 cDNAs. Nucleotides at positions 11, 20, and 33 in 66-1 not present in TC21 are shown, and the resulting changes in amino acid sequence are indicated. (2C) Sequence analysis flanking nucleotide position 215 showing the wild-type and mutant TC21 sequences. The adenine (hereinafter called "A") to thymine (hereinafter called "T") transversion in the second base pair of codon 72 of the TC21 oncogene is boxed.

DETAILED DESCRIPTION OF THE INVENTION

Figure 1A:
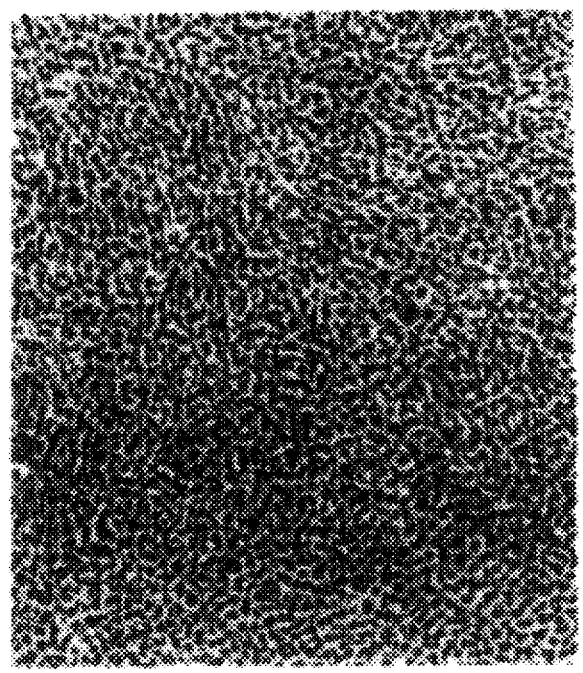
FIG. 1. Transformed focus induced by rescued plasmid 66-1. Approximately $1.5 \times 10^5$ NIH/3T3 cells were transfected with 0.01 mg of plasmid DNA. The morphology of a typical focus after two weeks in culture is shown.

The present invention utilizes an unusual and efficient cloning vector system which allows stable cDNA expression (Miki, et al., 1991). This system combines the ability to generate high complexity phagemid libraries containing a large proportion of full length cDNAs with the ability to perform efficient rescue of integrated plasmids (Miki, et al., 1989). In order to uncover novel human oncogenes by this strategy, an expression library was generated from an ovarian carcinoma line. The ovarian carcinoma cell line is a tumor type in which oncogenes were previously for the most part uncharacterized.

The present invention demonstrates the application of a stable expression cDNA cloning strategy in isolating new human oncogenes. One embodiment of the present invention is a novel oncogene, a mutated allele of TC21, which is a member of the ras superfamily. The TC21 oncogene of the present invention contains a position 72 substitution, resulting in the reduction of the intrinsic GTPase activity of the molecule. Other mutations clustered within this region will result in similar oncogenic activation. The TC21 oncogene is shown to activate oncogenic properties in tissue culture and in vivo, and to be present in the initially established human ovarian carcinoma line. Thus, the mutated TC21 allele of the present invention is likely activated as part of the malignant process in this tumor.

A striking finding was the lack of TC21 oncogene detection by standard NIH/3T3 transfection analysis using A2780 ovarian tumor cell line DNA. Such a standard transfection analysis incorporates genomic DNA fragments into the host cells. TC21 downstream signaling pathways in NIH/3T3 cells must be intact, because this oncogene was almost as efficient in transformation as an H-ras oncogene under analogous LTR transcriptional control. The TC21 oncogene including essential regulatory elements may be too large to allow efficient genomic transfer. Alternatively, species or tissue specific differences in transcriptional regulation of the genomic TC21 sequence may prevent a sufficient level of its expression for induction of the transformed phenotype.

The present discovery of new human oncogenes of the ras superfamily, which have evaded detection by previous approaches, raises the possibility that this oncogene may be widely implicated in human malignancies. The present finding that mutated TC21 exists in an ovarian cell line is significant, since this tumor-type has previously not been correlated with an activated ras-oncogene.

Two previous reports have examined the transforming capability of R-ras. These researchers attempted mutation of R-ras within the region of R-ras thought to inhibit GTPase activity. However, these experiments did not lead to the conversion of R-ras into a transforming factor. The inability of two previous reports to show both transforming (Lowe & Goeddel, 1987) or growth promoting (Rey et al., 1994) is contrary to the present invention, in which both position 38 and 87 mutants can efficiently induce morphological and malignant transformation in rodent fibroblasts. This disparity can be explained by potential experimental variations due to the use of different expression vectors of the higher susceptibility of NIH/3T3 cells to undergo transformation when compared to the Rat 1A cells used in the early study. These different results illustrate the unexpected nature of the present invention.

R-ras like TC21, is evolutionarily distant to H-ras, K-, or N-ras. But all of these proteins share a highly conserved N-terminal catalytic domain with effector binding sequences (amino acid sequence 32–40 in H-ras) (Valencia et al, 1991). Of all the small GTP-binding proteins with transforming activity in rodent fibroblasts, there exists a hierarchy of transforming ability with mutant H-ras gene displaying the highest potency of transforming properties. The second most potent transforming factor was the position 72 mutant of TC21 and yet weaker as a transforming factor were the two mutants of R-ras. This gradation of transforming potential is correlated with the efficiency and morphological parameters associated with cellular transformation. These marked differences among small G-proteins may reflect their relative ability in inducing downstream signaling cascade leading to cellular transformation.

The fact that the position 87 mutation of R-ras was stronger than the position 38 mutation in inducing transformation is also an unexpected result. In the case of H-ras, glycine 12 (gly38 in R-ras) is situated in the phosphate-binding domain and Mg2+ binding site in the first half of the guanine nucleotide binding domain and glutamine 61 (gln87 in R-ras) was postulated to be involved in interacting with a water molecule believed to attack the γ-phosphate (Valencia et al., 1991). Mutations in both positions of the ras oncogenes have been shown to abolish their GTPase activity leading to a GTP-bound, constitutively active state. The oncogenicity of both R-ras mutants analyzed in this study is most likely due to their GTPase deficiency, however, we do not exclude the possibility of impaired interaction with regulator molecules such as GTPase-activating proteins (GAP), guanine-nucleotide exchange stimulators or downstream effector elements such Raf (Boguski & McCormick, 1993).

The present finding that mutant TC21 and mutant R-ras can be oncogenic, in combination with the knowledge that particular sites within ras genes, when mutated are highly oncogenic ("hot spots") (Bos, 1989), leads to the conclusion that analogous mutations within hot spots of TC21 and R-ras will be oncogenic. Within TC21, mutations clustered around codon positions 23 to 75 are expected to have oncogenic properties. While within R-ras, mutations clustered around codon positions 38 to 87 are expected to have oncogenic properties. These mutational hot spots could not have been predicted prior to the present invention, since there was no suggestion that mutants of R-ras or TC21 would be oncogenic.

It has been reported that the C-terminal 60 amino acid region of the R-ras encoded product interacts with the Bcl-2 oncogene product both in vitro and in vivo (Fernandez-Sarabia & Bischoff, 1993). It was speculated that R-ras gene product may be involved in mediating the process of programmed cell-death and that Bcl-2 blocks this pathway. The present invention, in contradistinction, provides strong evidence that R-ras gene product when in the activated state can, in fact, efficiently promote cell growth and transformation. Whether R-ras plays a role in providing signals for cell survival remains to be determined.

The prevalent view of human carcinogenesis postulates a multi-step process involving the activation of cellular proto-oncogenes and inactivation of tumor suppressor genes (Weinberg, 1991). Tumor suppressor genes, such as, p53 and more recently, p16, have been implicated in more than 50% of all human cancer (Kamb et al., 1994). In contrast, oncogenes have yet to be commonly detected in many human tumors. These include ovarian, breast and prostate tumors as well as melanomas. Previously identified ras oncogenes have been implicated in a wide array of human malignancies (Bos, 1989). Greater than 90% of pancreatic carcinomas and more than 50% of colon carcinomas exhibit activating mutations of Hor K-ras alleles. In contrast, N-ras oncogenes seem to be preferentially observed in mesenchymal and hematopoietic malignancies. The novel oncogenes of the present invention provide two more additional targets for mutational activation. The wide spectrum of tissue expression of the R-ras transcripts provides strong impetus for identifying R-ras mutations in diverse human tumor types.

The presence of specific marker genes has important implications with respect to diagnosis and prognosis (Muss, et al., 1994). The oncogenes of the present invention provide a marker for identifying and diagnosing the transformation of cell populations in human tissues. These marker genes can serve as a prognostic marker in determining initial cell transformation, severity of tumors, tumor-progression and tumor relapse.

The mutant R-ras and TC21 can be detected either at the protein level or the gene itself can be analyzed for diagnosis and prognosis. At the protein level, mutant R-ras or TC21 can be detected in cell populations by monitoring protein expression levels in cases where oncogenesis is concomitantly associated with overexpression of ras. Alternatively, mutant R-ras and mutant TC21 can be detected using immunoblotting or in situ immunostaining techniques.

In one embodiment, the mutant TC21 and/or R-ras can be detected by a mutant-specific monoclonal or polyclonal antibody (Stiles et al.; Kohler and Milstein, 1975). Production of such antibodies are within the skill in the art, in view of the present invention and are thus considered within the scope of the invention. A standard immunoassay can be used to detect mutant TC21 and mutant R-ras.

Another embodiment for detecting mutant R-ras and mutant TC21 protein in tumors or tissue samples utilizes an altered mobility assay (Srivastava, et al., 1985). This assay can be used to distinguish mutant ras proteins from wild-type based on an altered mobility through gel electrophoresis.

Yet another embodiment for diagnosing or prognosing cancers having an oncogenic R-ras or TC21 utilizes the gene itself. The mutant gene can be detected in tissue samples as well as in situ using a nucleic acid probe specific for the mutant form of R-ras and/or TC21.

Another embodiment for detecting mutant R-ras or mutant TC21 nucleic acid in tumors or tissue samples utilizes an RNase protection assay (Bos, 1989). This assay could be useful in distinguishing R-ras and TC21 mutants from wild-type ras by use of a nucleic acid probe spanning the mutated region within the gene. Upon treatment of the probe-RNA hybrid with RNase, the form containing the mis-match will be cleaved, thereby producing two fragments when analyzed by gel electrophoresis.

Mutant TC21 can be used as a marker gene for diagnosis of cell transformation in ovarian tissue. Mutant TC21 gene can be detected in ovarian tissue samples by single strand conformational polymorphism (Orita, et al., 1989a; Orita, et al., 1989b) R-ras genes can also be detected by SSCP.

In addition, the present invention identifies new cancers which are associated with novel oncogenic ras-related gene, so that inhibition of such cancers is now possible. Such treatments utilize specific inhibitors of ras, which mechanistically function in a variety of ways. One method of blocking oncogenic ras activity involves blocking the functional group of ras required for its association with the cell membrane. The cell membrane is the site where ras is thought to facilitate its signal transduction activity. Ras normally is myristylated. Blocking myristylation results in a ras protein incapable of making the necessary association with the cell wall to be functional. However, much like other conventional chemotherapeutics, such therapeutic treatment may have an adverse effect on normal cells.

EXAMPLES

The following methods were used in carrying out the experiments illustrative of the present invention. These experiments represent non-limiting examples of the present invention. Other embodiments would be readily apparent to the skilled artisan and are considered within the scope of the present invention.

Library Construction

A cDNA expression library was constructed as described in Miki, et al., 1989, from poly(A)+ RNA generously provided by Dr. G. Kruh, Fox Chase Cancer Center. cDNAs were inserted directionally into the λpCEV29 eukaryotic expression vector, which is a derivative of the λpCEV27 vector (Miki, et al., 1991). The λpCEV29 plasmid is essentially the same as λpCEV27, except that a pak1 restriction endonuclease site has been added for ease of plasmid rescue. For the purposes of the example experiments the two plasmids, λpCEV27 and λpCEV29 are interchangeable.

The λpCEV27 system was developed to clone cDNAs by means of stable phenotypic changes induced by a specific cDNA. Use of a λ-plasmid composite vector made it possible to generate high complexity cDNA libraries and to efficiently excise the plasmid from the stably integrated phagemid DNA. This phagemid vector contained several features including two SfiI sites for construction of cDNA libraries using the automatic directional cloning (ADC) method, an M-MLV LTR promoter suitable for cDNA expression in mammalian cells, the SV40 promoter-driven neo gene as a selectable marker, and multiple excision sites (MESS) for plasmid rescue from genomic DNA. The λpCEV27 system incorporated, in addition to the M-MTV LTR, the rat preproinsulin polyadenylation (polyA) signal downstream from the cDNA cloning site. In this vector, the bacterial neo gene was placed under the independent control of the SV40 early promoter and the SV40 late polyA signal for use in marker selection in mammalian cells. The bona fide promoter of the neo gene was removed so as to fuse the SV40 promoter directly to the neo structural gene.

The cDNA library consisting of $\sim 10^7$ individual phage clones was amplified by a standard plate lysate method for DNA transfection experiments. Focus identification and plasmid rescue procedures were performed as described (Miki, et al., 1991).

Cell Cultures

Cultures were maintained in Dulbecco's Modified Eagle's Medium (DMEM) supplemented with 10% calf serum (CS). NIH3T3 cells carrying different plasmid constructs were derived by transfecting $1.5 \times 10^5$ cells with 1.0 mg of DNA by the calcium phosphate precipitation method (Wigler, et al., 1977). Transfectants were selected in Geneticin (750 mg/ml) and passaged twice prior to characterization of growth properties in vitro and in vivo.

Cell Proliferation Assay

For analysis of proliferation in semi-solid medium, $1 \times 10^4$ and $1 \times 10^3$ cells were suspended in 0.4% agarose (SeaPlaque, FMC) in DMEM supplemented with 10% CS as described elsewhere (DiFiore, et al., 1987). Colonies were stained with p-iodonitrotetrazolium violet (Sigma) and scored after 2 weeks. For analysis of tumor forming capacity, around $1-5 \times 10^5$ cells were injected subcutaneously into athymic nude mice as described (Heidaran, et al., 1990). Tumor occurrence and size were monitored at least once weekly for 5 weeks.

Detection of Mutations

For the reverse transcriptasepolymerase chain reactions ("RT-PCR"), 10 mg of total RNA was reverse-transcribed by MuLV reverse transcriptase (Gibco-BRL) to synthesize first strand cDNAs with random oligonucleotide primers in a final reaction volume of 50 ml. 4 ml of the first strand reaction was used in a 50 ml PCR reaction with primers "A" (5' ATAGATGACAGAGCAGCCCGGCTA 3') (SEQ ID NO:6) and "B" (5' GATAGAGGCAGTTTTGAAGAAATC 3') (SEQ ID NO:7) under the following cycling conditions: 94° C., 1 min., 57° C., 2 min., and 72° C., 3 min. for 30 cycles. Reactions were separated on an 1.3% agarose gel and the 143 bp PCR-amplified products were extracted from the gel by a QIAEX kit (Qiagen). Purified fragments were then digested with BfaI enzyme (New England Biolab) and electrophoresis was performed on a 4% agarose gel. DNA fragments were then transferred onto a nitrocellulose membrane and hybridized to a [32P]-labeled oligonucleotide probe (tc26) under standard conditions (Maniatis, et al., 1982). Following stringency wash of the filter, membrane was exposed to X-ray film (Kodak) at −70° C. for 3 hours.

Site-directed mutagenesis

The human wild-type R-ras coding region (nucleotide 1-657) was generated by polymerase chain reaction (PCR) method from a human cDNA library with an BamHI-tagged (+) primer (5'-AAAGGATCCATGAGCAGCGGGGCGGCGTCCG-3') (p5) (SEQ ID NO:8) and an EcoRI-tagged (−) primer (5'-AAAGAATTCCTACAGCAGGACGCAGGGGCA-3') (p10) (SEQ ID NO:9). PCR amplified product was subcloned into the multiple cloning site of an eukaryotic expression vector, pCEV29 and was sequenced to confirm authenticity. The R-ras point mutants were generated from the wild-type construct using a two-step PCR method (Gak et al., 1992). First, complementary mutant oligonucleotides were designed for position 38 (5'-TCGTGGGCGGCGTCGGCGTGGGCAA-3') (SEQ ID NO:10) and position 87 (5'-GACACCGCGGGCCTGGAAGAGTTC) (SEQ ID NO:11) for PCR separately with the upstream p5 primer and the downstream p10 primer (see above) under the following conditions: 94° C., 1 min; 45° C., 1 min; 72° C., 2 min; 25 cycles. The two PCR products amplified for each position were mixed and used as templates for a subsequent PCR reaction using the p5 and p10 primers under the following conditions: 94° C., 1 min; 58° C., 2 min; 72° C., 3 min; 30 cycles. PCR products were digested with restriction enzymes and subcloned into pCEV29 vector.

Northern Analysis

Total RNA was isolated from cell lines by RNAzol solution (Cinn/Biotecx Labs. Int. Inc.) as described by the manufacturer. After separating samples by electrophoresis on 1% denaturing formaldehyde agarose gel, RNAs were transferred to nitrocellulose filters (Maniatis, et al., 1982). A tissue RNA blot was purchased from Clontech (Palo Alto, Calif.). Blots were hybridized at 42° C. for 12 hours with [32P]-labeled DNA probes in 40% formamide, 6× saline sodium citrate (SSC), 5× Denhardt's solution, 1% SDS, 10% dextran sulfate and sonicated salmon sperm DNA (50 mg/ml). After the hybridization reactions, filters were washed twice in 1× SSC and 0.1% SDS at room temperature and in 0.1×SSC and 0.1% SDS at 55° C. Filters were dried and exposed to X-ray films at −70° C. for various times.

In vitro transcription/translation

A TNT in vitro transcription/translation kit was purchased from Promega. Approximately 1 mg of circular plasmid was added to each reaction of rabbit reticulocyte lysate in the presence of 40 mCi of [35S] methionine (NEN, Dupont, 10 mCi/ml; specific activity, 1078 Ci/mmol) and Sp6 RNA polymerase in a final volume of 50 ml. Reaction mixtures were incubated at 30° C. for 90 minutes. Samples (5 ml) were then boiled in Laemmli sample buffer and protein products were resolved by 10% polyacrylamide gel electrophoresis (SDS-PAGE). Gels were dried and exposed to X-ray films at −70° C. for 6–12 hours.

Cell Proliferation assay

For analysis of proliferation in semi-solid medium, $1\times10^4$ and $1\times10^5$ cells were suspended in 0.5% agarose (SeaPlaque, FMC) in 10% CS as described in DiFiore et al., 1987. Colonies were stained and scored after 2 weeks. For analysis of tumor forming capacity, around $1.0\times10^5$ cells were injected subcutaneously into athymic nude mice as described (Heidaran et al., 1990). Tumor occurrence and size were monitored weekly.

Western blotting

Mass-selected cultures were lysed with HEPES solubilizing solution (50 mM HEPES, $Na_4PO_2$, 4 mM EDTA, 10% Triton X-100) and 100 mg of protein was loaded per lane on an 12.5% SDS-PAGE gel. Following transfer onto Immobilon-P membrane (Millipore, Bedford, Mass.), R-ras protein was detected by a Pan-ras monoclonal antibodies, M90 (Lacal, et al., 1986).

Example 1

Figure 1B:
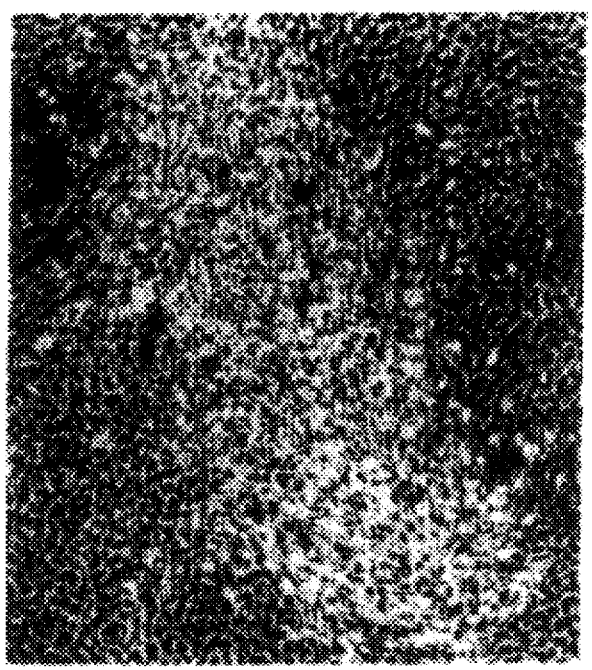

Expression Cloning of a Transforming Gene from a Human ovarian Tumor cDNA Library A λpCEV29 cDNA expression library was generated from a late passage of the A2780 cell line established from a metastatic human ovarian carcinoma (Eva, et al., 1982). For analysis of transforming cDNAs, library DNA was used to transfect NIH/3T3 cells. A distinct class of morphologically transformed foci consisting of rapidly-growing, highly retractile cells (FIG. 1) was identified at a frequency of about 1 focus-forming units per plate ("ffu/plate"). Two independent foci (64-1 and 66-1) from separate plates were isolated and shown to exhibit G418 resistance (a neomycin resistance detection agent), indicating that each had taken up and stably integrated the vector. Plasmid rescue was performed as described in Miki, et al. (1991), and the transforming cDNAs were identified based on their high-titred transforming activities ($>10^4$ffu/pmol) and ability to confer a similar transformed morphology.

Restriction enzyme analysis revealed cDNA inserts of 1.9 and 2.4 kb (kilobase pairs) for plasmids rescued from foci 64-1 and 66-1, respectively. Moreover, the two cDNA clones displayed the same pattern with BamHI, HindIII and XbaI restriction enzymes, suggesting that they were different cDNAs generated from the same gene (FIG. 2A). The nucleotide sequence of clone 66-1 revealed an open reading frame of 612 bp (base pairs) flanked by 6 bp and ~1.7 kb of 5'- and 3'-untranslated regions, respectively. The open reading frame predicted a protein species of 204 amino acids with a calculated molecular mass of ~23 kDa (kilodaltons) (FIG. 2A). A search in the GenBank Database uncovered extensive sequence identity to TC21, a member of the superfamily (Drivas, et al., 1990). TC21 was initially cloned from a human teratocarcinoma cDNA library by polymerase chain reaction (PCR) methodology using degenerate oligonucleotides to the conserved region of the ras genes (Drivas, et al., 1990).

Example 2

TC21 Oncogene is Point-Mutated at Codon 72

Detailed comparison between TC21 and 66-1 identified nucleotide sequence disparities in two regions of the coding sequence. First, three additional nucleotides were present at positions 11, 20, and 33 in the N-terminal region of 66-1 leading to frame-shifts, which resulted in replacement of amino acid residues from codons 5 to 10 (AGGRLR) in TC21 with (GWRDGSG) in 66-1 (FIG. 2B). However, the addition of these three base pairs restored the reading frame at amino acid position 12 of TC21. Our sequence determined for 66-1 was identical to that of a cDNA clone which we isolated from a normal human epithelial cell library, indicating that this region was identical in both the 66-1 oncogene and wild-type allele. Thus, we attribute differences from that reported for TC21 in this region (Drivas, et al., 1990) to sequencing variations arising from the high GC content in this region.

Figure 2C:
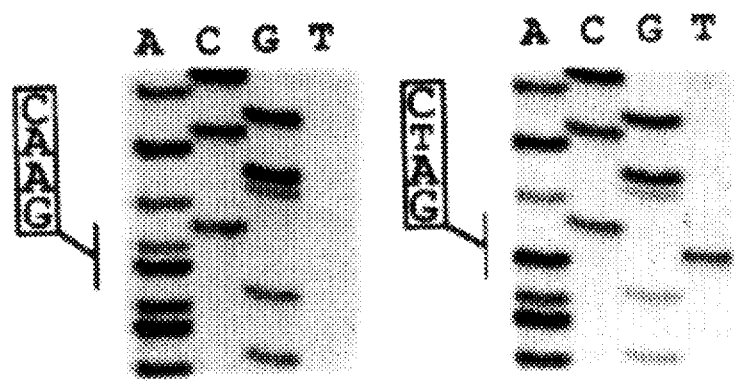
Figure 8:
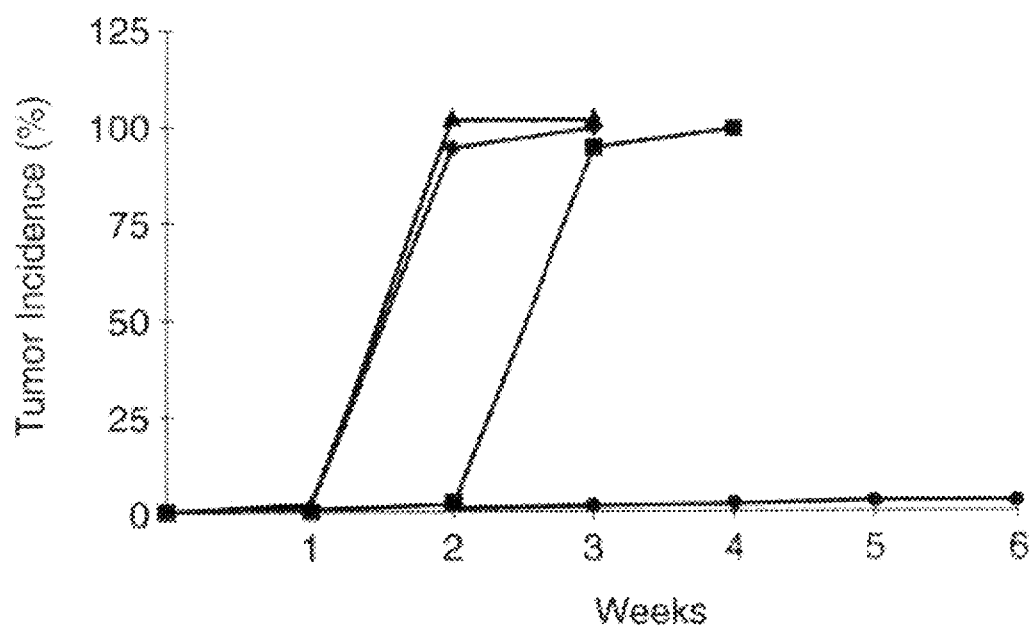
FIG. 8. Tumorigenicity of R-ras mutants. $\sim 1.0 \times 10^5$ cells were introduced subcutaneously into athymic nude mice. 7 mice were used for tumorigenicity assay for each transfectant. Data indicates incidence of tumors at the week after inoculation.

The second disparity involved a region in which the sequences of both the TC21 and the normal human epithelial cell cDNA were identical. This alteration involved an A:T to T:A transversion in the second nucleotide of codon 72, resulting in the substitution of glutamine (CAA) by leucine (CTA) in the 66-1 oncogene (FIG. 2C). Gln72 corresponds exactly to Gln61 in the Harvey-ras (H-ras) proto-oncogene product, a position frequently mutated and responsible for activation of the H-ras oncogene in a variety of human tumors (Yuasa, et al., 1983; Bos, 1989). The same mutational alteration was also present in clone 64-1, indicating that both transforming cDNAs were derived from transcripts expressed from a point-mutated allele of the wild-type TC21 gene.

Example 3
Codon 72 Mutation Activates TC21 Oncogenicity

In order to assess the effects of the single A to T transversion on TC21 biological properties, we compared transforming activities of the normal and mutant cDNAs by NIH/3T3 transfection analysis. As shown in Table 1, the mutant exhibited transforming activity of $>10^4$ ffu/pmol when either 64-1 or 66-1 plasmids were used. In striking contrast, the wild-type TC21 allele expressed under the influence of the same promoter showed no detectable transforming activity.

These results established the mutation as being responsible for TC21 oncogene activation. Table 1 shows that the TC21 oncogene was almost as active as an H-ras oncogene. However, the wild-type H-ras allele was significantly more active than the wild-type TC21 (Table 1). We next analyzed mass populations of marker-selected cells for other properties of transformed cells including growth in semi-solid agar-containing medium and tumorigenicity upon subcutaneous inoculation of athymic nude mice. Cells expressing the TC21 mutant exhibited a highly transformed phenotype, inducing colony formation in agar and tumors in animals at efficiencies comparable to those of cells expressing an oncogenically activated H-ras mutant (Table 1). All these findings established that the mutation was responsible for activation of TC21 oncogenic properties in transfected NIH/3T3 cells.

TABLE 1

Transforming Properties of the 66-1 Oncogene

| Transfectant | Transforming efficiency[a] (ffu/pmol) | Soft-agar colony formation[b] (%) | Tumorigenicity[c] (no. tumors/no inoculated) |
|---|---|---|---|
| pSVneo | $<1.0 \times 10^0$ | <1.0 | 0/6 |
| H-ras$^{wt}$ | $2.5 \times 10^2$ | ND | ND |
| H-ras$^{val12}$ | $5.0 \times 10^4$ | 23.6 | 7/7 |
| TC21$^{wt}$ | $<1.0 \times 10^0$ | ND | ND |
| TC21$^{leu72}$ | $6.0 \times 10^4$ | 21.6 | 7/7 |

[a]NIH3T3 cells were transfected with different amounts of each plasmid DNA and the number of foci scored after 3 weeks in culture. All 3 plasmid DNAs produced similar numbers of marker selectable colonies (~$10^4$ colonies/μg).
[b]NIH/3T3 cells were transfected with 1 μg of each plasmid, and mass populations were marker-selected. Each marker-selected culture was suspended in 0.4% semi-solid agarose in medium supplemented with 10% CS. Colonies of more than 300 cells were scored after 14 days and results represent means values of duplicate plates.
[c]~4 × $10^4$ marker-selected cells were inoculated subcutaneously into athymic nude mice. Animals were monitored at least twice weekly for 5 weeks for the appearance of >0.5 cm$^2$ tumors at the inoculation site.
[d]The 64-1 and 66-1 plasmids exhibited similar transforming efficiencies.
ND-not determined.

A2780 ovarian tumor cells contain the TC21 codon 72 mutation

Figure 3A:
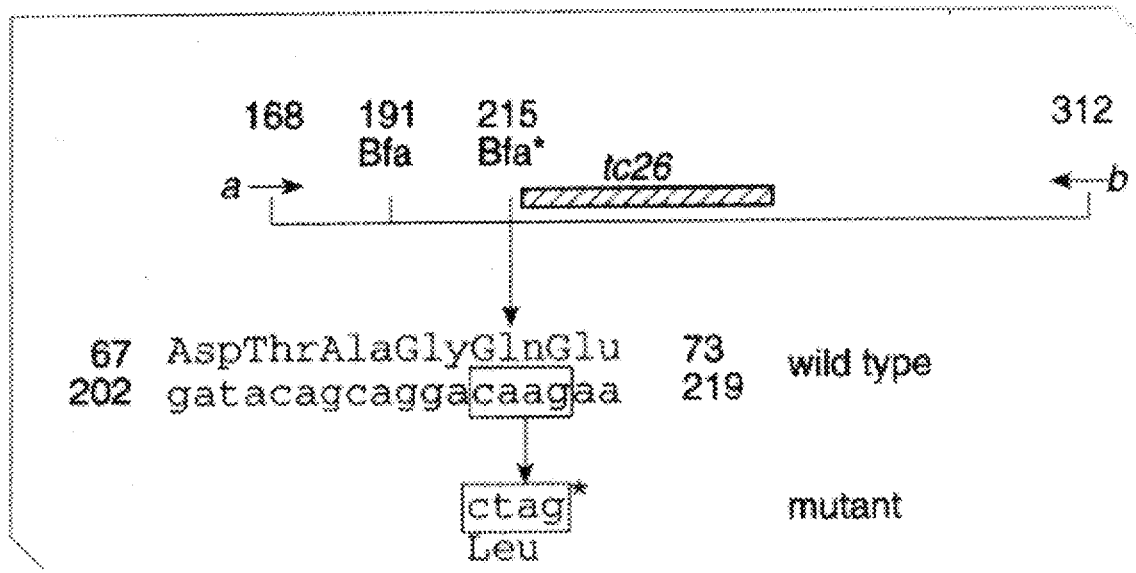
FIGS. 3A & 3B. Detection of TC21 mutation in A2780 human ovarian carcinoma cells. (3A) Schematic representation of the strategy for detection of mutations at position 215 by PCR showing primers a and b (arrows) used for amplification of the region between positions 168 to 312. The polymorphic BfaI site generated as a result of the A to T transversion at position 215 is indicated by an asterisk. An additional BfaI site at position 191, which serves as an internal control for restriction enzyme digestion, is also shown. The shaded bar represents the 45 bp oligonucleotide probe, tc26, used for detection of mutant-specific restriction fragments. (3B) Southern analysis of BfaI digested PCR fragments generated from RNA samples derived from AB589 human mammary epithelial cells, A2780 ovarian carcinoma cells at early (E), medium (M), and late (L) passages, and the SK-ES-1 human Ewing's sarcoma cell line (Nishida & Gotoh, 1993). Samples were subjected to Southern blot analysis and hybridized with the tc26 probe. The 95 bp mutant-specific fragment, the 143 bp band representing uncut DNA, and the 119 bp band representing the wild-type specific fragment obtained by digestion at position 191 alone, are indicated.

To establish that the codon 72 mutation was present in the ovarian tumor cell line, advantage was taken of the creation of a polymorphic restriction enzyme site, BfaI (C/TAG), when an A:T to T:A transversion occurs in the second base pair of the tetranucleotide wild-type sequence (CAAG) (FIG. 3A). PCR primers flanking the mutation site were generated to produce an amplified product of 143 bp. An additional BfaI site 24 bp upstream from Gln$^{72}$ was included in the PCR product to serve as an internal control for the restriction enzyme reaction. Total cellular RNAs were prepared from 3 different A2780 lines corresponding to early (A2780E, ~20), middle (A2780M, ~50), and late (A2780L, >200) passage cells. In parallel, control cell RNAs were prepared from a normal mammary epithelial cell line, AB589, a Ewing's sarcoma cell line, SK-ES-1, and NIH/3T3 cells transformed by the 66-1 plasmid.

Figure 3B:
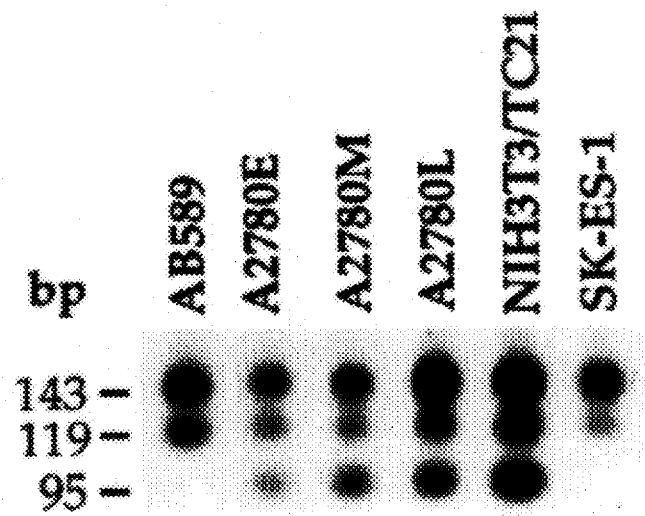

As shown in FIG. 3B, two DNA fragments were observed in samples derived from normal human cells and Ewing's sarcoma cells. The upper 143 bp band represented undigested DNA, and the lower 119 bp band represented the product generated by cleavage at the internal control BfaI site. The restriction fragments produced by BfaI digestion of the PCR product from 66-1 transformed NIH/3T3 cells contained an additional 95 bp fragment, consistent with the size expected if cleavage occurred at both control and polymorphic BfaI sites (FIG. 3B). This 95 bp mutant-specific restriction fragment was also observed in all 3 passages of the A2780 tumor cell line, indicating that the TC21 gene was oncogenically activated in the initially established human ovarian cancer line.

Example 5
Lack of Transforming Activity of A2780 Genomic DNA

To investigate the detectability of the mutant TC21 oncogene within A2780 tumor cells by standard genomic transfer, we performed transfection experiments with high molecular weight DNAs isolated from both A2780E and A2780L cells. As controls, genomic DNAs were prepared from T24/EJ bladder carcinoma cells containing a mutated H-ras oncogene and NIH/3T3 cells transfected with the TC21 oncogene cDNA. As shown in Table 2, genomic DNAs isolated from EJ as well as TC21 transformed NIH/3T3 cells induced transformed foci at comparable efficiencies (20–50 ffu/plate). In striking contrast, A2780 genomic DNAs showed no detectable focus forming activity in several experiments. These results establish that the TC21 oncogene would have evaded detection by standard genomic DNA mediated gene transfer approaches.

TABLE 2

Transforming Activities of Different Genomic DNAs

| | | Transforming efficiency[a] (ffu/pmol) | | |
|---|---|---|---|---|
| DNA Source | Oncogene | exp. 1 | exp. 2 | exp. 3 |
| EJ | H-ras$^{val12}$ | ~30 | 30, 25, 30 | 20, 25 |
| 66-1 transfected NIH/3T3 | TC21$^{leu72}$ | ~50 | ND | 30, 30, 50, 50 |
| A2708$^E$ | TC21$^{leu72}$ | 0, 0, 0, 0 | 0, 0, 0, 0, 0 | 0, 0 |
| A2780$^L$ | TC21$^{leu72}$ | 0, 0, 0, 0 | ND | 0, 0, 0, 0 |

[a]NIH3T3 cells were transfected with different 50 μg of each genomic DNA per plate, and the number of foci were scored after 3 weeks in culture. Data shown here were generated from 3 independent experiments, and each number represents results from a single plate.
ND-not determined.

Example 6
Expression of TC21 Transcripts

Figure 4A:
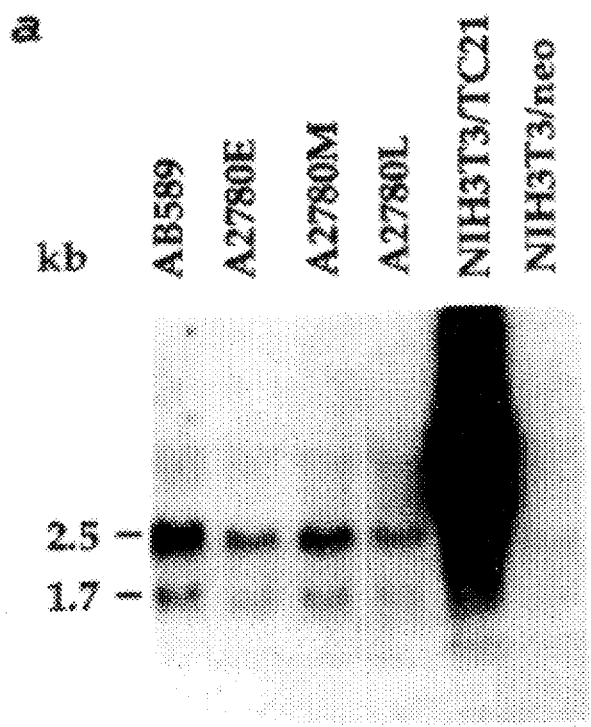
FIGS. 4A & 4B. TC21 expression of in cell lines and tissues. (4A) Northern analysis of total cellular RNA obtained from a AB589 human mammary epithelial cells, early, medium, and late passages of A2780 cells (A2780E, A2780M, A2780L), and NIH/3T3 cells transfected with the TC21 transforming plasmid (NIH3T3/TC21) or with control plasmid, pSV2neo (NIH3T3/neo). Approximately 20 mg of total cellular RNA was subjected to Northern blot analysis using a [32P]-labeled TC21 cDNA probe. A major 2.5 kb and a minor 1.7 kb TC21 transcript are indicated. Equal amounts of RNA were loaded in each lane as confirmed by ethidium bromide staining. (4B) Expression of TC21 gene in tissues was analyzed utilizing a commercially available filter (Clontech, Palo Alto) with approximately 2 mg of poly(A)+ RNA loaded in each lane. Following hybridization with a TC21 cDNA probe, the filter was stripped and rehybridized with a control mouse β-actin probe for normalization of the amount of RNA loaded.
Figure 4B:
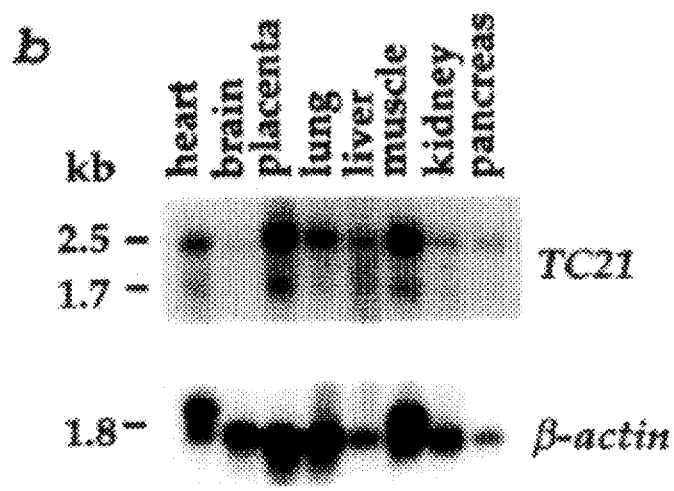

We sought to characterize TC21 transcripts present in normal cells and the A2780 ovarian tumor line. FIG. 4A demonstrates expression of a major 2.5 kb and minor 1.7 kb transcript in A2780 cells at each of several different passage levels. TC21 transcripts of the same respective mobilities were observed at similar relative levels in AB589 human epithelial cells. Thus, oncogene activation was not associated with any gross mRNA size alterations. It should be noted that the 2.4 kb cDNA isolated by expression cloning must represent essentially the full length major transcript. NIH/3T3 cells also expressed two TC21 transcripts of similar respective sizes at somewhat lower but detectable levels. FIG. 4B shows that the two TC21 transcripts were ubiquitously present in all human tissues examined with the highest levels in heart, placenta, and skeletal muscle. Moderate levels were detected in lung and liver, while low levels were observed in brain, kidney, and pancreas.

Example 7
Construction of R-ras mutant plasmids

Figure 5:
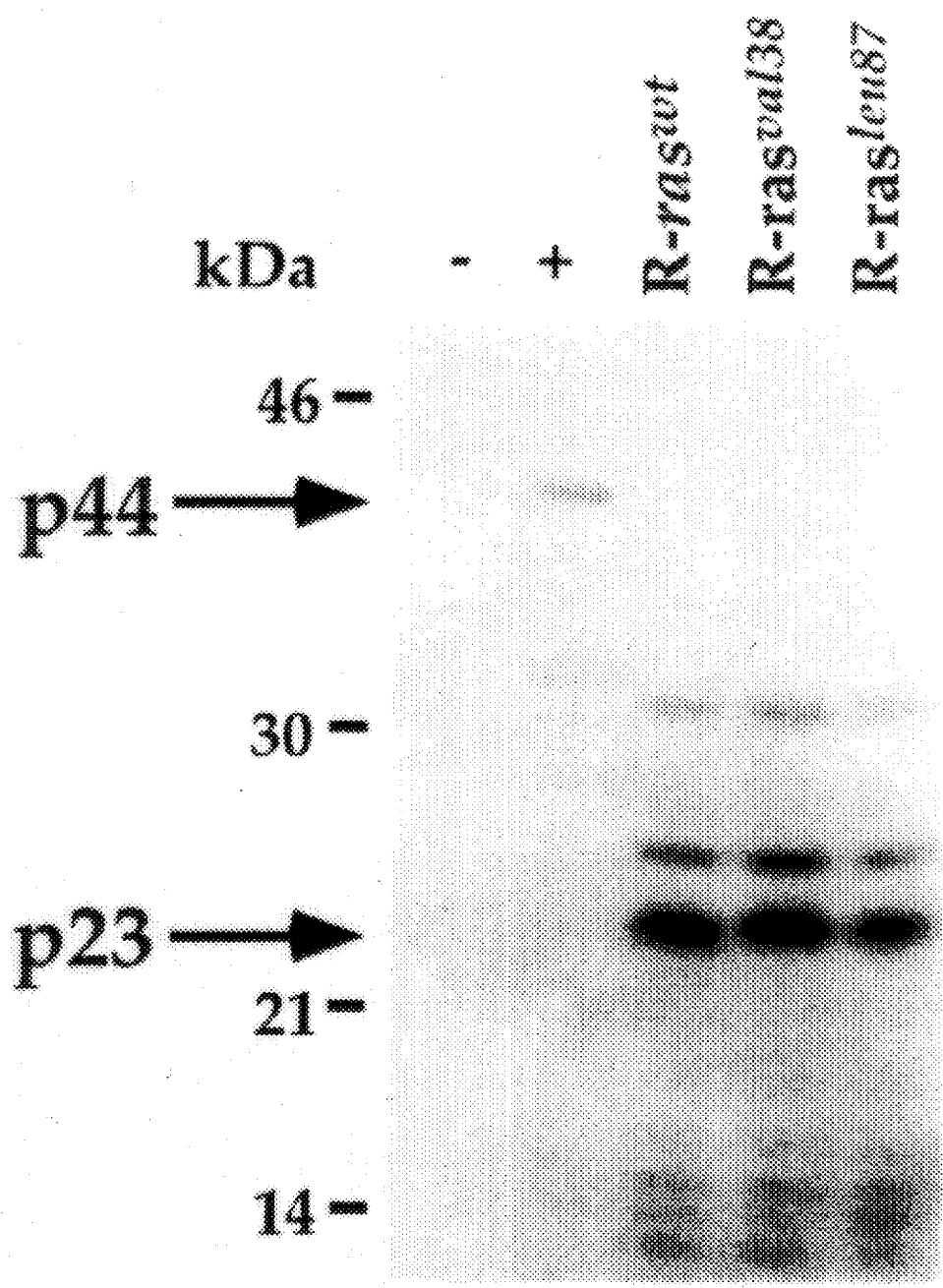
FIG. 5. In vitro transcription/translation of R-ras mutant plasmids. Samples with 1 mg of circular plasmid DNAs from wild-type (R-ras$^{wt}$), position 38 (R-ras$^{val38}$) and position 87 (R-ras$^{leu87}$) mutants of R-ras gene were in vitro transcribed and translated with rabbit reticulocyte lysate in the presence of [35S]methionine. Controlled reactions were performed with either no DNA added (−) or with a Ga12 plasmid that has previously been described (Chan et al., 1993). The 23-kDa and 44-kDa protein species encoded by R-ras and Ga12 cDNAs, respectively, are indicated by arrows.

Previous studies failed to demonstrate that R-ras was capable of transforming activity in Rat-1A fibroblasts (Lowe & Goeddel, 1987). We sought to examine this finding by generating codon 87 (position 61 in H-ras) as well as codon 38 (position 12 in H-ras) mutants for focus formation assay in NIH/3T3 fibroblasts. A guanine ("G") to thymine ("T") base substitution was introduced by polymerase chain reaction (PCR) at the second base pair of codon 38, replacing glycine (GGC) with a valine (GTC) residue (R-$^{val38}$). Similarly, the glutamine (CAG) residue at position 87 was replaced by a leucine (CTG) residue through an A to T transition (R-$^{leu87}$). Analogous mutations in the human oncogenes have been commonly detected in human tumor samples (Bos, 1989). Each R-ras mutant as well as the wild-type allele were subcloned into an eukaryotic expression vector, pCEV29 under the transcriptional control of a MuLV Long Terminal Repeat (LTR) promoter. To ascertain the integrity of our constructs and to detect the putative products generated from each plasmid, cDNA sequences were in vitro transcribed and translated in the presence of [35S] methionine. As shown in FIG. 5, protein species of ~23 kilodalton (kDa) were observed in samples derived from wild-type and mutant plasmids, consistent with the predicted size of the human R-ras gene product. It might be noted that while the present example shows specific mutations, it is contemplated that other amino acid mutations would provide similar results.

Example 8
Transforming properties of R-ras mutants

Figure 6A:
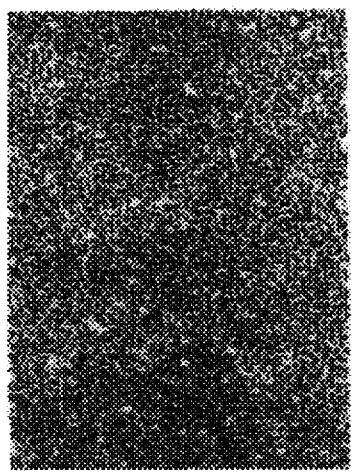
FIG. 6. Focus morphology of NIH/3T3 transfectants. Expression plasmids representing R-ras$^{wt}$, R-ras$^{val38}$, and R-ras$^{leu87}$ constructions were transfected separately into NIH/3T3 cells, and morphologically transformed foci were photographed after 2 weeks in culture.
Figure 6B:
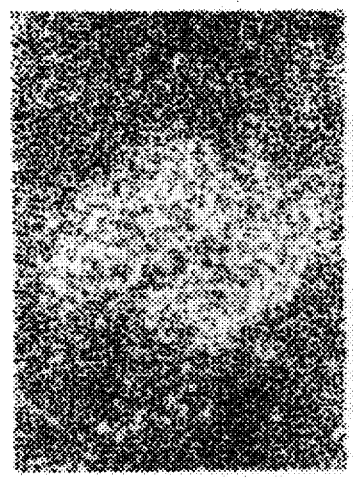
Figure 6C:
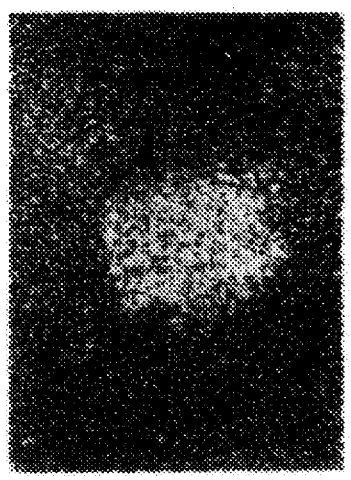

To examine the transforming potential of our cDNA clones, plasmid DNAs carrying various ras constructs were transfected into NIH/3T3 cells by the calcium phosphate precipitation method (Wigler et al., 1977). As controls, parallel cultures were transfected with pSV2neo, the wild-type (H-ras$^{wt}$) or a valine 12 mutant (H-ras$^{val12}$) of the H-ras gene. We also included both wild-type (TC21$^{wt}$) and mutant (TC21$^{leu87}$) forms of TC21 gene. As shown in Table 3, both R-ras$^{val38}$ and R-ras$^{leu87}$ DNAs demonstrated high titered focus forming ability ($10^3$–$10^4$ ffu/mg) with transformed cells appearing within 10 days following transfection. Among the mutant ras-related genes examined, H-ras$^{val12}$ possessed the highest specific transforming activity, followed by TC21$^{leu72}$ and further lowered transforming activity was observed with the two R-ras mutants. In addition, R-ras mutant foci displayed morphological features that were distinct from the classical ras transformed foci. Position 87 mutant induced foci exhibited an overall dense, rounded appearance and were comprised of small, rounded and highly retractile cells (FIG. 6). In contrast, position 38 mutant induced foci were characterized by areas of high cell density with flatter and less refractile cells. Of note, no transformed foci were observed in cultures transfected with an R-ras$^{wt}$ construct, whereas the wild-type H-ras$^{wt}$ gene driven by a similar promoter produced ~$10^5$ ffu/mg of focus forming efficiency.

TABLE 3

Transforming Properties of Expression Plasmids

| Plasmid | Transforming efficiency* (ffu/μg) | Colony-forming efficiency (cfu/μg) | Specific transforming activity (ffu/cfu) |
| --- | --- | --- | --- |
| pSV2neo | <1.0 × 10$^0$ | 1.0 × 10$^4$ | >10$^{-4}$ |
| H-ras$^{wt}$ | 1.0 × 10$^3$ | 1.0 × 10$^5$ | 0.01 |
| H-ras$^{val12}$ | 3.0 × 10$^4$ | 2.0 × 10$^4$ | 1.5 |
| TC21$^{wt}$ | <1.0 × 10$^0$ | 1.0 × 10$^5$ | <10–5 |
| TC21$^{Leu72}$ | 1.0 × 10$^5$ | 3.0 × 10$^5$ | 0.3 |
| R-ras$^{wt}$ | <1.0 × 10$^0$ | 1.0 × 10$^5$ | <10–5 |
| R-ras$^{val38}$ | 2.0 × 10$^3$ | 1.0 × 10$^5$ | 0.02 |
| R-ras$^{Leu87}$ | 1.0 × 10$^4$ | 1.0 × 10$^5$ | 0.1 |

*NIH3T3 cells were transfected with various concentrations of each plasmid and number of foci was scored after 3 weeks in cultures. All plasmids are of equivalent sizes.

To demonstrate that the R-ras mutants induced a transformed phenotype typical of classical oncogenes, marker-selected mass cultures were generated for in vitro and in vivo analysis. R-ras$^{val38}$ and R-ras$^{leu87}$ transfected NIH/3T3 cells formed large, progressively growing colonies in soft agar at high frequency. In contrast, NIH/3T3 cells transfected with R-ras$^{wt}$ and control pSV2neo produced significantly lower numbers of colonies. Inoculation of R-ras$^{val38}$ or R-ras$^{leu87}$ transfectants subcutaneously into athymic nude mice induced tumors at high frequency within three weeks. In contrast, no tumors were observed with pSV2neo control cells as late as 7 weeks. All of these data provided strong evidence that codon 38 and 87 mutants of the R-ras gene can function as oncogenes, inducing morphological and malignant transformation both in vitro and in vivo.

Example 9
Expression of the R-ras gene product in transformants

Figure 7A:
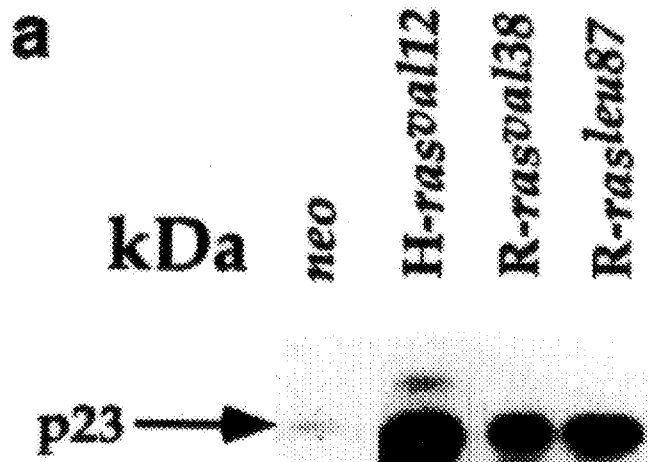
FIGS. 7A & 7B. Expression of R-ras. (7A) Cell lysates derived from NIH/3T3 cells transfected with various expression plasmids were analyzed by Western blotting techniques. Approximately 100 mg of total cell protein was loaded per lane and immunoblotted with a pan-ras monoclonal antibodies, M90. The 23-kDa protein species of R-ras are indicated by an arrow. (7B) Tissue distribution of R-ras transcripts was examined utilizing a commercially available nitrocellulose filter (Clontech) with about 2 mg of poly(A) +RNAs derived from various human tissues. [32P]-labeled R-ras cDNA probe was hybridized to the filter and the amount of RNA loaded was normalized with a mouse β-actin probe. The 4.6- and 1.2-kb transcripts of R-ras are indicated.

To identify the R-ras protein product in R-ras transformed cells, marker-selected mass cultures were subjected to Western analysis using a Pan-ras antibody, M90 (Lacal, et al., 1986) that recognizes the R-ras gene product. As shown in FIG. 7A, M90 antibodies cross-reacted efficiently with H-ras p21 proteins. Similarly, R-ras p23 gene products were also readily detected in cells transfected with either mutant R-ras plasmids to a level ~50-fold higher than in cells transfected with the pSV2neo .

Figure 7B:
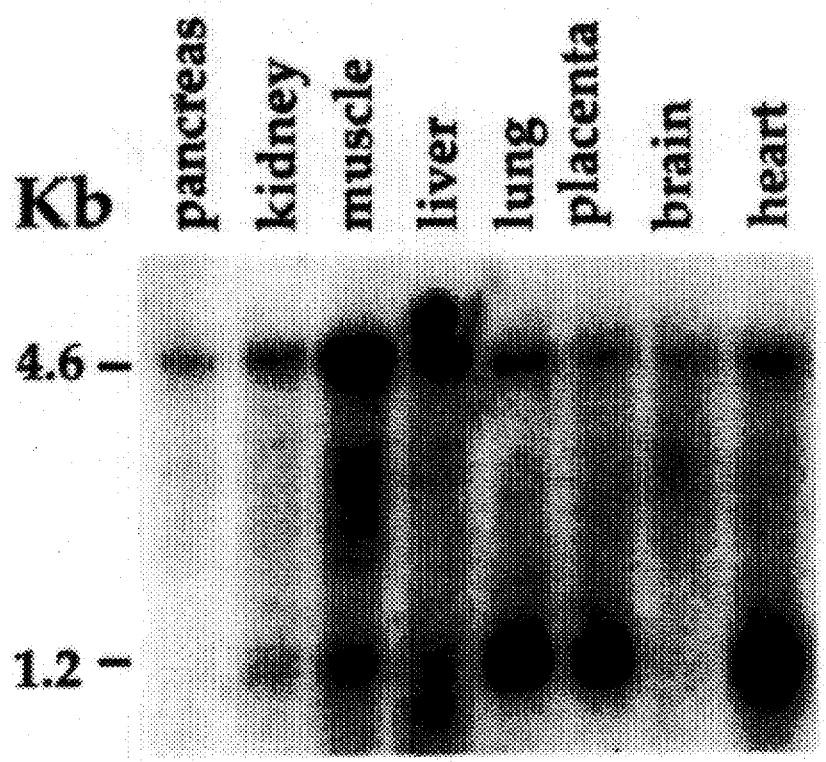

To search for cell types in which R-ras gene was preferentially expressed, Northern blot analysis was performed with poly(A)+RNA isolated from a wide spectrum of human tissues. As shown in FIG. 7B, the 4.6 kb and 1.2 kb transcripts of the R-ras gene, which may derive from alternative splicing events, were ubiquitously expressed in all tissues examined. Interestingly, the relative ratio of these two transcripts varied widely in different tissue types with the larger 4.6 kb transcript expressed at a higher level in skeletal muscle and the smaller 1.2 kb transcript preferentially overexpressed in heart.

Example 10
Cooperation between R-ras and c-raf-1

A previous study demonstrated the cooperative effect of H-ras and c-raf-1 genes in transforming NIH/3T3 cells (Cuadrado et al., 1993). To test whether R-ras shares downstream effectors with H-ras, co-transfection experiments were performed with the c-raf-1 plasmid and either the R-ras$^{wt}$ or R-ras$^{val38}$ plasmids. As controls, analogous experiments were performed using the H-ras$^{wt}$ gene under control of its own promoter so as to give a low level of focus-forming frequency (10–20 ffu/plate). As shown in Table 4, whereas the c-raf-1 plasmid alone did not yield detectable transformed foci, co-transfection with 0.1 mg of the H-ras$^{wt}$ construct increased the number of ras transformed foci by 4 to 5 fold. We were unable to detect any transformed foci upon co-transfection of c-raf-1 and R-ras$^{wt}$. However, when a sub-threshold level (1 ng) of R-ras$^{val38}$ was used in the co-transfection experiments with c-raf-1, we observed a marked increase in focus formation efficiency of >15 ffu/plate. This cooperative effect was reproducibly obtained in a separate experiment with quantitative enhancement of focus-forming-units with increasing amount of R-ras$^{val38}$ plasmid.

TABLE 4

Analysis of cooperative transformation of NIH/3T3 cells by R-ras and c-raf-1*

| | Exp. 1 | | | Exp. 2 | |
|---|---|---|---|---|---|
| | — | pCEV29 | c-raf-1 | — | c-raf-1 |
| H-ras$^{wt}$ (0.1 µg) | 10 | 1, 0 | 50, 50 | 15 | 60, 70 |
| H-ras$^{wt}$ (1.0 µg) | 0, 0 | 0, 0 | 0, 0 | ND | ND |
| R-ras$^{val38}$ (5 ng) | ND | ND | ND | 0 | 21, 26 |
| R-ras$^{val38}$ (1 ng) | 0, 0 | 0, 0 | 15, 20 | 0 | 2, 4 |

*H-ras or R-ras plasmids at indicated amounts were co-transfected with either no plasmid (—) or 1.0 µg each of pCEV29 or c-raf-1 expression plasmids. The number of focus forming unit produced in each plate from two separate experiments is indicated.
ND - not determined.

Example 11

To screen for mutations of TC21 and R-ras genes in human tumor samples, we have a sensitive polymerase chain reaction (PCR) based single-stranded conformation polymorphism (SSCP) analysis (Orita, et al., 1989; Orita, et al., 1989) that could detect single base alterations in DNA samples. Briefly, PCR primers flanking hot spots (positions 24 and 72 of TC21; positions 38 and 37 of R-ras of both genes are used to amplify those regions from human tumor DNA samples and analyze on a denaturing polyacrylamide gel. Changes in base compositions due to mutational alteration theoretically modify the physical structure and therefore other the mobility of the amplified single-stranded DNA when comparing to the wild-type sequence.

Based on this method, we are able, using plasmids corresponding to both wild-type and position 72 mutant alleles of TC21, to generate optimal conditions for SSCP analysis with the observation of distinct mobility shift for both wild-type and mutant sequences. We are developing conditions for SSCP analysis of other positions in TC21 as well as R-ras.

The hereinbelow list of references provides a complete citation of each of the references cited hereinabove. All of the references mentioned in the present application are incorporated in toto into this application by reference thereto.

References

Barbacid, M. (1987) Annu. Rev. Biochem. 56, 779–827.
Boguski, M. S. & McCormick, F. (1993). Nature, 366, 643–653.
Bos, J. (1989) Cancer Res. 49, 4682–4689.
Chan, A. M.-L., Fleming, T. P., McGovern, E. S., Chedid, M., Miki, T. & Aaronson, S. A. (1993). Oncogene 13, 762–768.
Chardin, P. (1991) Cancer Cell 3, 117–126.
Cuadrado, A., Bruder, J. T., Heidaran M. A., App, H., Rapp, U. R. & Aaronson, S. A. (1993). Oncogene 8, 2443–2448.
DiFiore, P. P., Pierce, J. H., Fleming, T. P., Hazan, R., Ullrich, A., King, C. R., Schlessinger, J. & Aaronson, S. A. (1987) Cell 51, 1063–1070.
Drivas, G. T., Shih, A., Coutavas, E., Rush, M. G. & D'eustachio, P. (1990) Mol. Cell. Biol. 10, 1793–1798.
Eva, A., Robbins, K. C., Andersen, P. R., Srinivasan, A., Tronick, S. R., Reddy, E. P., Ellmore, N. W., Galen, A. T., Lautenberger, J. A., Papas, T. S., Westin, E. H., Wong-Staal, F., Gallo, R. C. & Aaronson, S. A. (1982) Nature 295, 116–119. Fernandez-Sarabia, M. J. & Bischoff, J. R. (1993). Nature 366, 274–275.
Gak, E., Taylor, W. G., Chan, A. M.-L. & Rubin, J. S. (1992). FEBS Letts. 311, 1, 17–21.
Kamb, A., Gruis, N. A., Weaver-Feldhaus, J., Liu Q., Harshman, K., Tavtigian, S. V., Stockert, E., Day III, R. S., Johnson, B. E. & Skolnick, M. H. (1994). Science 264, 436–439.
Kitayama, H., Sugimoto, Y., Matsuzaki, T., Ikawa, Y. & Noda, M. (1989). Cell 56, 77–84.
Kohler and Milstein, (1975) Nature 256, 495–497.
Heidaran, M. A., Fleming, T. P., Bottaro, D. P., Bell, G. I., Di Fiore, P. P. & Aaronson, S. A. (1990) Oncogene 5, 1265–1270.
Lacal, J. C., Aaronson, S. A. (1986) Proc. Natl. Acad. Sci. U.S.A. 83, 5400–5404.
Lowe, D. G., Capon, D. J., Delwart, E., Sakaguchi, A. Y., Naylor, S. L. & Goeddel, D. V. (1987) Cell 48, 137–146.
Lowe, D. G. & Goeddel, D. V. (1987) Mol. Cell. Biol. 7, 2845–2856.
Maniatis, T., Fritsch, E. F. & Sambrook, J. (1982) Molecular Cloning: a Laboratory Manual. Cold Spring Harbor Laboratory, Cold Spring Harbor, N.Y.
Miki, T., Fleming, T. P., Crescenzi, M., Molly, C. J., Blam, S. B., Reynolds, S. H. & Aaronson, S. A. (1991) Proc. Natl. Acad. Sci. U.S.A. 88, 5167–5171.
Miki, T., Matsui, T., Heidaran, M. & Aaronson, S. A. (1989) Gene 83, 137–146.
Muss, H. B., Thor, A. D., Berry, D. A., Kute, T., Liu, E. T., Koerner, F., Cirrincione, C. T., Budman, D. R., Wood, W. C., Barcos, M., Hendersen, I. C. (1994) N. Engl. J. Med., 330, 1260-L.
Nishida, E. & Gotoh, Y. (1993) TIBS 18, 128–131.
Novick, P. & Brennwald, P. (1993). Cell 70, 597–601.
Orita, M., Iwahana, H., Kanazawa, H., Hayashi, K., Sekiya, T. (1989a) Detection of polymorphisms of human DNA gel electrophoresis as single-strand conformation polymorphisms. Proc. Natl. Acad. Sci. USA 86, 2766–2770.
Orita, M., Suzuki, Y., Sekiya, T., Hayashi, K. (1989D) Rapid and sensitive detection of point mutations and DNA polymorphisms using the polymerase chain reaction. Genomics 5, 874–879.
Rey, I., Taylor-Harris, P., Van Erp, H. & Hall, A. (1994). Oncogene 9, 685–692.
Ridley, A. J., Paterson, H. F., Johnston, C. L., Diekmann, D. & Hall, A. (1992). Cell 70, 401–410.
Ridley, A. J. & Hall, A. (1992). Cell 70, 389–399.
Stiles, et al., editors, Basic and Clinic Immunology, (Lange Medical Publications, Los Altos, Calif., Fourth edition).
Srivastava, Aaronson, S. A., (1985) Proc. Natl. Acad. Sci. U.S.A., 82, 38–42.

Valencia A., Chardin, P., Wittinghofer A. & Sander C. (1991). *Biochemistry* 30, 19, 4648–4654.
Weinberg, R. A. (1991) *Science* 254, 1138–1146.
Wigler, M., Silverstein, S., Lee, L. S., Pellicer, A., Cheng, Y. C. & Axel, R. (1977) *Cell* 11, 223–232.

Yuasa, Y., Srivastava, S. K., Dunn, C. Y., Rhim, J. S., Reddy, E. P. & Aaronson, S. A. (1983) *Nature* 303, 775–779.

We claim:

1. An isolated DNA encoding a TC21 mutant protein (SEQ ID NO:5) capable of neoplastic transformation of cells wherein said mutation is at amino acid position 72.

2. An isolated DNA encoding a TC21 mutant protein according to claim 1, wherein said mutation at amino acid position 72 is a substitution of a glutamine with a leucine.

3. An isolated DNA encoding a TC21 mutant protein according to claim 1 wherein said mutation comprises an A:T to T:A transversion at a second nucleotide position of codon 72.

4. An isolated DNA encoding a TC21 mutant protein according to claim 1 wherein said mutation comprises an addition of an amino acid residue within the region of codons 5–10.

5. An isolated DNA according to claim 4 wherein said codons 5–10 are replaced with Gly-Trp-Arg-Asp-Gly-Ser-Gly.

6. An isolated DNA encoding a mutant TC21 protein, said protein having an amino acid sequence of SEQ ID NO:4.

7. A diagnostic kit comprising:
   a probe specific for mutant TC21 DNA according to claim 1; and
   a container containing said probe.

* * * * *